United States Patent
Miller et al.

(10) Patent No.: US 10,058,579 B2
(45) Date of Patent: Aug. 28, 2018

(54) DIETARY SUPPLEMENTS CONTAINING EXTRACTS OF CINNAMON AND METHODS OF USING SAME TO PROMOTE ENHANCED SIRTUIN, CELL AND TELOMERE INTEGRITY

(75) Inventors: Peter J. Miller, Broomfield, CO (US); Tim Romero, Sarasota, FL (US); Bolin Qin, Gaithersburg, MD (US); Augustin T. Romero, Spring Hill, TN (US)

(73) Assignee: IN Ingredients, Inc., Columbia, TN (US)

( * ) Notice: Subject to any disclaimer, the term of this patent is extended or adjusted under 35 U.S.C. 154(b) by 945 days.

(21) Appl. No.: 13/699,779

(22) PCT Filed: May 26, 2011

(86) PCT No.: PCT/US2011/038175
§ 371 (c)(1),
(2), (4) Date: Nov. 26, 2012

(87) PCT Pub. No.: WO2011/150229
PCT Pub. Date: Dec. 1, 2011

(65) Prior Publication Data
US 2013/0072574 A1    Mar. 21, 2013

Related U.S. Application Data

(60) Provisional application No. 61/348,657, filed on May 26, 2010.

(51) Int. Cl.
*A61K 36/54*    (2006.01)
*A61K 31/07*    (2006.01)
(Continued)

(52) U.S. Cl.
CPC ............ *A61K 36/54* (2013.01); *A23L 33/105* (2016.08); *A61K 31/07* (2013.01); *A61K 31/185* (2013.01);
(Continued)

(58) Field of Classification Search
None
See application file for complete search history.

(56) References Cited

U.S. PATENT DOCUMENTS

2003/0017998 A1*  1/2003  Snow et al. .................... 514/27
2007/0190114 A1*  8/2007  Smart .......................... 424/440
(Continued)

FOREIGN PATENT DOCUMENTS

WO        2011/150229        12/2011

OTHER PUBLICATIONS

Westphal et al. A therapeutic role for sirtuins in diseases of aging? TRENDS in Biochemical Sciences, vol. 32, No. 12. Nov. 5, 2007.*
(Continued)

*Primary Examiner* — Anna Pagonakis
(74) *Attorney, Agent, or Firm* — Dinsmore & Shohl LLP

(57) ABSTRACT

A dietary supplement composition is provided for enhancing the expression of a sirtuin gene or protein. An inventive supplement composition includes at least one cinnamon extract containing at least 0.5% doubly linked Type-A polymers by dry weight. The cinnamon extract is derived from the *Cinnamonum aromaticum, Cinnamonum verum* or *Cinnamonum burmannii* plant. In some embodiments, the cinnamon extract is present at approximately 20%-50% of the dry weight of the composition. A vitamin, weight loss agent, or antioxidant is optionally provided in the composition. The dietary supplement composition is administered orally to promote expression or enhanced expression of a sirtuin gene or protein.

10 Claims, 13 Drawing Sheets

(51) Int. Cl.
    A61K 31/185    (2006.01)
    A61K 31/59     (2006.01)
    A61K 45/06     (2006.01)
    A23L 33/105    (2016.01)

(52) U.S. Cl.
    CPC .............. *A61K 31/59* (2013.01); *A61K 45/06* (2013.01); *A23V 2002/00* (2013.01)

(56) References Cited

U.S. PATENT DOCUMENTS

| 2007/0196520 | A1  | 8/2007  | Lin et al. |
| 2008/0057088 | A1* | 3/2008  | Blass et al. .................. 424/401 |
| 2008/0279786 | A1  | 11/2008 | Cash |
| 2009/0087501 | A1  | 4/2009  | Cummins |

OTHER PUBLICATIONS

Baxter, Richard. Anti-aging properties of resveratrol: review and report of a potent new antioxidant skin care formulation. Journal of Cosmetic Dermatology, 7, 2-7, 2008.*

International Search Report and Written Opinion of PCT/US2011/038175 (WO/2011/150229) published Jan. 12, 2011.

Yamamoto, H. et al., "Sirtuin Functions in Health and Disease," Molecular Endocrinology 21(8): 1745-1755, Apr. 24, 2007.

Anderson, R. et al., "Isolation and Characterization of Polyphenol Type-A Polymers from Cinnamon with Insulin-like Biological Activity," J. Agric. Food Chem., 52, 65-70, 2004.

Dang, W. et al., "Histone H4 lysine-16 acetylation regulates cellular lifespan," Nature, 459(7248): 802-807, Jun. 11, 2009.

Firestein, Ron et al., "The SIRT1 Deacetylase Suppresses Intestinal Tumorigenesis and Colon Cancer Growth," PLoS ONE, vol. 3, Issue 4, 1-9, Apr. 2008.

Kaeberlein, M. et al., "The SIR2/3/4 complex and SIR2 alone promote longevity in *Saccharomyces cerevisiae* by two different mechanisms," Genes & Development, 13:2570-2580 (1999).

Lagouge, M., Resveratrol Improves Mitochondrial Function and Protects against Metabolic Disease by Activating SIRT1 and PGC-1a, Cell 127, 1109-1122, Dec. 15, 2006.

Rogina, B. et al., "Longevity Regulation by *Drosophila* Rpd3 Deacetylase and Caloric Restriction," Science, vol. 298, 1745, Nov. 29, 2002.

Rutanen, J. et al., "SIRT1 mRNA Expression May be Associated With Energy Expenditure and Insulin Sensitivity," Diabetes, vol. 59, 829-835, Apr. 2010.

Kennedy, B., "Daughter Cells of *Saccharomyces cerevisiae* from Old Mothers Display a Reduced Life Span," The Journal of Cell Biology, vol. 127, No. 6, Part 2, 1985-1993, Dec. 1994.

Satoh, A. et al., "SIRT1 Promotes the Central Adaptive Response to Diet Restriction through Activation of the Dorsomedial and Lateral Nuclei of the Hypothalamus," The Journal of Neuroscience, 30(30): 10220-10232, Jul. 28, 2010.

Shang, Q., et al., "Colesevelam improves insulin resistance in a diet-induced obesity (F-DIO) rat model by increasing the release of GLP-1," Am J Physiol Gastrointest Liver Physiol 298: G419-G424, 2010.

Trillou, R. et al., "Anti-obesity effect of SR141716, a CB1 receptor antagonist, in diet-induced obese mice," Am J Physiol Regul Integr Comp Physiol 284: R345-R353, 2003.

Veyrat-Durebex, C., "The Lou/C rat: a model of spontaneous food restriction associated with improved insulin sensitivity and decreased lipid storage in adipose tissue," Am J Physiol Endocrinol Metab, 296: E1120-E1132, 2009.

* cited by examiner

DIETARY SUPPLEMENTS CONTAINING EXTRACTS OF CINNAMON AND METHODS OF USING SAME TO PROMOTE ENHANCED SIRTUIN, CELL AND TELOMERE INTEGRITY

CROSS-REFERENCE TO RELATED APPLICATION

This application depends from and claims priority to U.S. Provisional Application No. 61/348,657 filed May 26, 2010, the entire contents of which are incorporated herein by reference.

FIELD OF THE INVENTION

The present invention relates to dietary supplement compositions containing cinnamon extracts and methods for promoting enhanced SIRTUIN, cell and telomere integrity.

BACKGROUND OF THE INVENTION

Longevity and lifespan have increased over the centuries thanks to improvements in medicine, nutrition, and the environment. Though these all are major contributors to a longer lifespan, another key factor is the regulation and expression of certain genetic factors and how they affect cellular function and proliferation, which vary from one individual to another. Damages to an organism's chromosomes throughout life are a major cause of aging and susceptibility to age related diseases such as cancers, Parkinson's disease, and Alzheimer's disease.

It has been shown that within a unique group of advanced age individuals, the centenarians who are people at or over the age of a hundred, a relatively slow increase in the frequency of some types of chromosomal aberrations are observed. Several studies confirm that these people have better efficiency of DNA repair or elimination of these unwanted cells (Bolognesi et al., *Cancer Epidemiol. Biomark. Prev.*, 1997; 6:249-256; Wojda et al., *Cancer Epidemiol. Biomark. Prev.*, 1997; 6:249-256; Zietkiewicz et al., *Journal of Applied Genetics*, 2009; 50(3):pp. 261-273).

The length of the telomere section of chromosomes, also called the "cap," is related to longevity. As an organism ages the length of these "cap" regions shorten with every cellular division. This is particularly evident in peripheral blood leukocytes that have long telomeres at birth but by the second decade of life a drastically eroded and continue eroding throughout life at a slower pace (Calado, et al., *PLoS One*. 2009 Nov. 20; 4(11):e7926). As telomere caps shorten, the chromosomes become more prone to instability causing aneuploidy (an abnormal number of chromosomes), translocation (movement of chromosomal parts to a normative location in the genome), and mutations or deletions to genetic material (Calado, *PLoS One*. 2009 Nov. 20; 4(11): e7926). Gene instability and alterations in gene expression have been found to be hallmarks of eukaryotic aging (Oberdoerffer et al., *Cell*, 2008 Nov. 28; 135(5):907-18).

Unlike stem cells and some cancerous cells that have the ability to synthesize and use telomerase (a telomere lengthening enzyme), most somatic cells endure progressively shorter telomeres. Through senescence even adult stem cells that possess this ability are not able to overcome the inevitable loss contributing to human aging (Aubert, and Lansdorp, *Physiol Rev*. 2008 April; 88(2):557-79). Goto et al. identified that the effect of pro-inflammatory substances produced by the innate immune system may physiologically or pathologically contribute to aging. Pro-inflammatory signals once beneficial in the earlier stages of life may be harmful and antagonistically affect an individual in the later stages of life.

The aforementioned causes of aging can be attenuated by use of longevity prolonging substances such as resveratrol (3,5,4'-trihydroxy-trans-stilbene). These compounds act by simulating the expression of a particular category of enzymes, the sirtuins 1-7 or SIRTs, which are 299 to 555 amino acid long proteins. The SIRTs are a nicotinamide adenine dinucleotide (NAD+) dependent deacetylases that remove acetyl groups ($—C_2H_3O^+$) from a variety of proteins, either activating or deactivating them by doing so.

Several SIRTs are localized to particular cellular compartments and tissue. Illustratively, SIRT2 is predominantly found expressed in the brain (Voelter-Mahlknecht et al., Int J. Oncol. 2005 November; 27(5):1187-96) and SIRT5 expression is predominately in the mitochondria of cardiac muscle cells (Mahlknecht et al., *Cytogenet Genome Res*. 2006; 112(3-4):208-12). While most of the SIRTs possess a life prolonging effect, currently the most studied is SIRT1.

Sirtuin-1 has many functional roles in the mammalian organism such as its ability to regulate metabolic function and gene expression. Aerobic capacity and mitochondrial oxidative phosphorylation have a great effect on longevity, neurodegenerative diseases like Alzheimer's, Parkinson's, and Huntington's disease and are tightly linked to mitochondrial dysfunction. It has been shown that SIRT1 activation promotes proper mitochondrial function and energy and metabolic homeostasis by increasing PGC-1 activation, a key regulator of energy metabolism (Lagouge et al., *Cell*. 2006 Dec. 15; 127(6):1109-22; Liang et al., 2006; Rasouri et al., *Med Sci (Paris)*. 2007 October; 23(10):840-4).

SIRT1 has been indicated in causing an autophagic effect in cells, autophagy is a process in which the cell recycles unnecessary cellular components through lysosomal degradation and reuses the material for new processes necessary to survival, which can help prolong an organism's life (Morselli et al., *Autophagy*. 2010 January; 6(1):186-8). The inhibition of enzymes such as PARP-1 (Poly[ADP-ribose] Polymerase 1), which can mediate cell death devoid of DNA damage may be crucial to longevity. SIRT1 is able to deacetylate and inactivate the active form of PARP-1, directly affecting its enzymatic activity. Also, SIRT1 can indirectly affect PARP activity by negatively regulating the promoter of PARP-1 gene (Rajamohan et al., *Mol Cell Biol*. 2009 August; 29(15):4116-29). SIRT-1 was also found to relocalize itself to damaged DNA to promote repair mechanisms, decreasing the amount of aberrations to chromosomes (Oberdoerffer et al., *Cell*, 2008 Nov. 28; 135(5):907-18).

Ablation of SIRT1 in murine liver tissue disrupted fatty acid oxidation and elevated cellular stress and pro-inflammatory cytokines, increasing cellular damage eventually leading to cell death. It is apparent that SIRT1 is necessary for proper liver function and can inhibit the over production of pro-inflammatory factors, possibly reducing the harmful effects they can have on an aging organism (Purushotham et al., Cell Metab. 2009 April; 9(4):327-38). A study by Alcendor et al. (*Circ Res*. 2007 May 25; 100(10):1512-21) using mice that over expressed SIRT1 in cardiac tissue demonstrates that moderate overexpression of SIRT1 can have a protective effect on the heart, attenuating oxidative stress and age-dependent increases in hypertrophy, apoptosis/fibrosis, mitochondrial dysfunction and also decreased the expression of senescent markers, i.e. INK4/ARF expression.

Another gene in the sirtuin family associated with increasing longevity is SIRT3. SIRT3 is typically localized in the mitochondria of cells but has also been found to be exported out of the mitochondria possibly for other functions or degradation. While in the mitochondrial SIRT3 plays a large role in cellular metabolism, it activates acetyl-CoA synthetase by deacetylation and also activates glutamate dehydrogenase and isocitrate dehydrogenase-2 by deacetylation, all of which are key regulators of metabolism (Allison et al., *Cell Cycle.* 2007 Nov. 1; 6(21):2669-77; Schlicker et al., *J Mol. Biol.* 2008 Oct. 10; 382(3):790-801). The overexpression on SIRT3 may also be linked to increased longevity. Illustratively, Sundaresan et al. (*Mol Cell Biol.* 2008 October; 28(20):6384-401) found SIRT3 overexpression to be stress responsive and protective of cardiac muscle cells from genotoxic and oxidative stress. The authors found this is accomplished by the sirtuin's ability to deacetylate the Ku70 protein. The deacetylated Ku70 protein can then associate itself with the proapoptotic protein Bax, making cells resistant to Bax-mediated cell death.

In model organisms such as mice and *drosophila*, underexpression of SIRTs appears to be detrimental to the organism's longevity (Bellizzi et al., *Genomics.* 2005 February; 85(2):258-63). The moderate overexpression of all the sirtuin genes can be beneficial for increasing longevity. Sirtuin-7 is typically expressed in the nucleus of cells and interacts with histones and RNA polymerase-1 (Ford et al., 2007). The overexpression of SIRT7 has been shown to increase the transcription of ribosomal DNA by RNA polymerase-1 increasing the amount of protein being translated and promoting proliferation. Depletion of SIRT7 stops proliferation, triggers apoptosis and greatly reduces RNA pol-1 activity signifying that SIRT7 is required for cell viability (Ford et al., 2007).

The mammalian sirtuins (SIRT1-SIRT7) are implicated in gene silencing, mitochondrial function, energy homeostasis, insulin sensitivity, and longevity (Yamamoto et al., *Mol. Endocrinol,* 2007; 21:1745-1755). Sirtuins (SIRTs) are longevity factors that appear to regulate critical cardio-protective pathways in the mammalian heart. Three family members, SIRT1, SIRT3, and SIRT7, block stress-induced cardiac hypertrophy (Schug et al., *Aging* (Albany N.Y.). 2010 Mar. 31; 2(3):129-32). SIRTs regulate metabolism and life span. Insulin resistance and subclinical atherosclerosis are associated with SIRT1 downregulation in monocytes. Glucotoxicity and lypotoxicity play a relevant role in quenching SIRT1 expression (de Kreutzenberg et al., *Diabetes.* 2010 April; 59(4):1006-15).

Type 2 diabetes is characterized by a combination of defective insulin secretion and insulin resistance that results from a progressive age-associated decline in β cell function. A recent study has reported that a reduction in SIRT1 activity with age contributes to this age-related impairment of β-cell function (Ramsey et al., *Aging Cell.* 2008 January; 7(1):78-88).

Longevity can be optimized by adoption of a healthy diet and life-style, including moderate exercise, a decrease in food intake together with a healthy diet, and elimination of smoking and other disease causing factors (Marques et al., *Maturitas.* 2010 February; 65(2):87-91). Calorie restriction (CR) has been reported to increase SIRT1 protein levels in mice, rats, and humans, and elevated activity of SIRT1 orthologs extends life span in yeast, worms, and flies.

Thus, there exists a need for compositions and methods of improving sirtuin expression or activity to promote improved longevity and decreased disease.

SUMMARY OF THE INVENTION

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description.

The present invention provides a dietary supplement composition including extracts of cinnamon containing at least 0.5% Type-A polymers by dry weight.

The present invention provides a dietary supplement composition including a *Cinnamonum Aromaticum, Cinnamonum Verum,* or *Cinnamonum Burmannii* (collectively *Cinnamonum*) extract containing at least 0.5% singly or doubly linked Type-A polymers. The *Cinnamonum* extract is optionally approximately 20-50% of the dry weight of the composition. Other vitamins, antioxidants, or sirtuin enhancing agents can also be included in the dietary supplement composition.

The present invention provides processes for enhancing cell survival and telomere structural integrity, increasing the expression of a gene encoding a sirtuin, increasing the expression of a SIRT protein, preventing diet induced obesity, or increasing insulin sensitivity in a subject. The processes include administering composition including a *Cinnamomum* extract containing at least 0.5% doubly linked Type-A-Polymers by dry weight, wherein the *Cinnamomum* extract is approximately 0.01%-99.9% if the dry weight of the composition.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF EMBODIMENTS OF THE INVENTION

Figure 1:
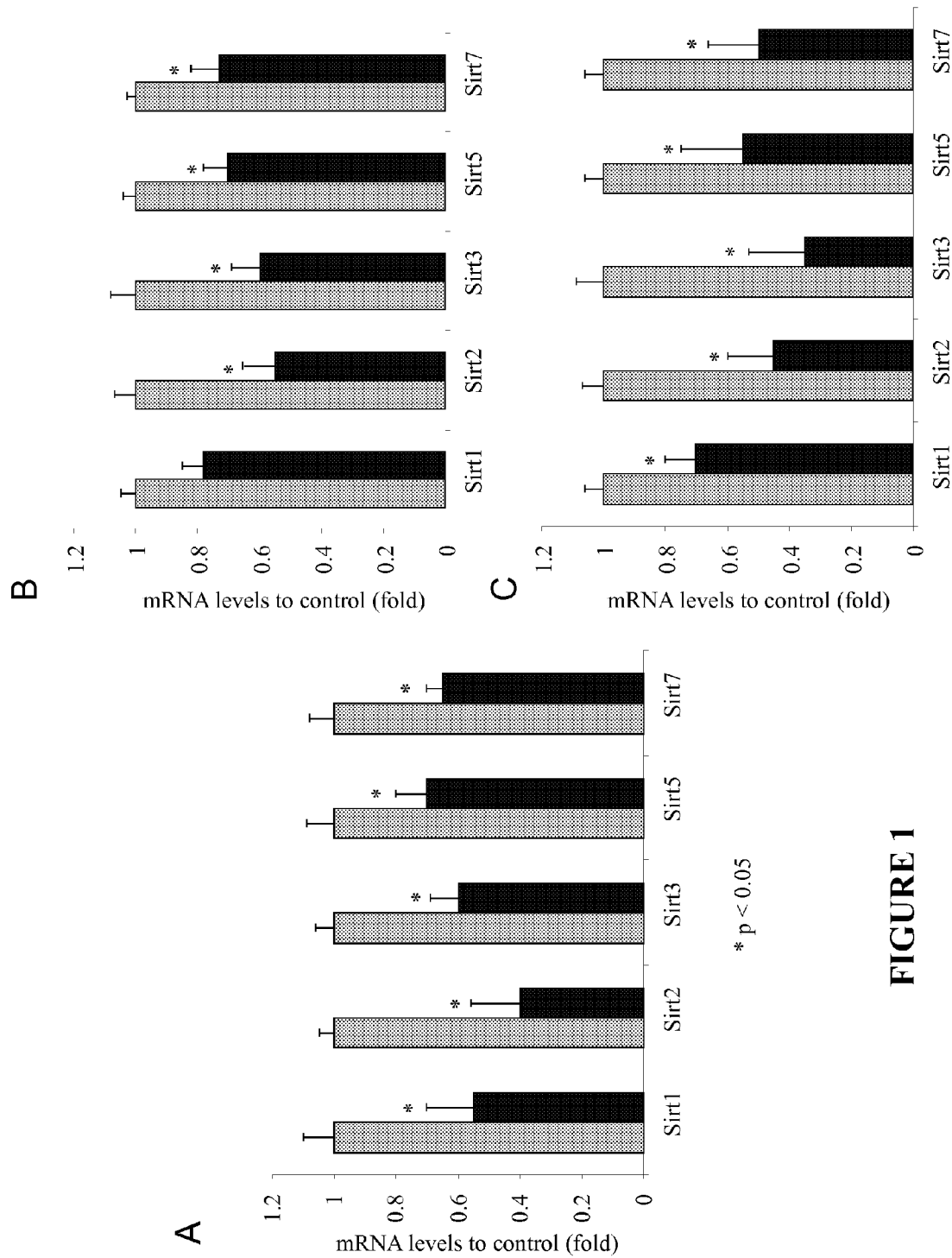
FIG. 1 represents SIRT mRNA levels in adipose tissue (A), small intestine (B), and liver (C), and effects caused by a high fructose diet feeding, which induced a systemic insulin resistance, dyslipidemia and metabolic syndrome.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only.

The present invention advantageously has utility as a cinnamon extract composition that promotes the expression of genes encoding SIRTs, expression of SIRTs, enhanced cell structural integrity, and telomere integrity. Compositions and processes are provided that increase the expression of SIRTs and are useful for enhancing cell and organism vitality. The invention provides materials in the form of botanical extracts, such as extracts of cinnamon that have utility for altering the expression level of sirtuin genes or proteins in subjects.

The cinnamon extract dietary supplement may be in pharmaceutical dietary supplement compositions in solid, semi-solid, or liquid dosage forms, such as, for example, tablets, chewables, suppositories, pills, capsules, powders, liquids, or suspensions, and may be provided in unit dosages suitable for a single administration. Time release preparations are also contemplated as effective dosage formulations. The compositions may include an effective amount of a selected extract of *Cinnamonum* in combination with a pharmaceutically acceptable carrier and, in addition, may include other medicinal agents, pharmaceutical agents, carriers, or diluents.

"Polyphenol" refers to a group of chemical substances found in plants, characterized by the presence of more than one phenol group per molecule. For purposes of this disclosure, it is to be understood that polyphenols include, but are not limited to, Type-A polymers and oligomers or phenolic materials. Research indicates that a class of polyphenol has antioxidant characteristics with potential health benefits. Sources of polyphenols include green tea, white tea, red wine, dark chocolate, olive oil, and other fruits, vegetables, and plants including cinnamon.

"Polyphenol Type-A polymers" are the bioactive type of polymers in the cinnamon extracts. They are identified by their protonated molecular masses as A-type singly or doubly linked procyanidin oligomers of the catechins and/or epicatechins. The polymers are composed of monomeric units. (Anderson et al., *J. Agric. Food Chem.*, 2004; 52:65-70.) Illustrative examples of olyphenol type-A polymers include the procyanidin oligomers of the catechins and/or epicatechins. Oligomers may have masses ranging from 576 to 1728 Da and may include a trimer, tetramer, and mixture of oligomers, respectively. Doubly doubly linked procyanidin type-A polymers have the strucutre:

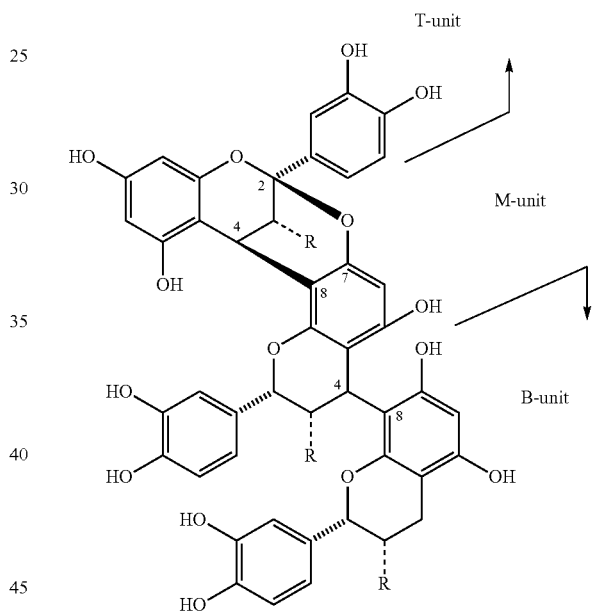

where ⸺ OH=(+) catechin and ◄ OH=(−) epicatechin.

The term "enhancing" is defined as an increase in expression, activity, or effect relative to a control related to the presence of an effector such as an extract of cinnamon or a component thereof. Illustrative examples of enhanced are increases in the expression level or rate of one or more genes that encode a sirtuin, or increases in levels of a sirtuin protein.

"Active ingredient" refers a component present in the cinnamon extract which renders, directly or indirectly, the intended effect of the cinnamon extract. One particular example is a polyphenol type-A polymer, with more particular examples being singly linked type-A polymers and doubly linked type-A polymers.

Cinnamon may be obtained from various resources. Illustratively, cinnamon is obtained from bark. Cinnamon bark may be obtained from various parts of the world, including China, Sri Lanka, Indonesia and others. An extract of cinnamon is optionally derived from any *Cinnamonum* species. In an exemplary embodiment, an extract of cinnamon is derived from the bark of *Cinnamonum aromaticum*, *Cinnamonum verum*, or *Cinnamomum burmannii*. In some embodiments, an extract of cinnamon is derived from the bark of the *Cinnamomum zeylanicum* tree of the genus *Lauraceae*. This tree is native to eastern and southeastern Asia. Other sources of cinnamon may also be used in the methods and materials disclosed herein. Cinnamon bark may be used in the form of raw bark, sliced, or minced bark, or pulverized bark for the preparation of the therapeutic materials, and pulverized cinnamon bark is used in particular instances. In some embodiments, the *Cinnamonum* raw material or extract contains between 0.01%-100% singly or doubly linked Type-A polymers by dry weight.

Extraction and Drying Method

Extracts may be prepared by various methods. The extracts are optionally water soluble. As such, the extracts are optionally water soluble water extracts, water soluble alcohol extracts, or water soluble extracts of other operative extraction processes. The extraction process is directly linked to the final composition of the resulting extract. As such, a product formed by one process does not necessarily equate to an extract formed by a separate process, often differing by a single extraction parameter. The processes described herein represent exemplary methods to produce extracts with the desired level of the active agent-polyphenols.

Extraction parameters such as water quality, heating temperature, drying temperature, heating time, drying time, and filtering processes all contribute to the quality and efficiency of the process. Water quality directly affects the concentration of active compounds. Poor quality water may cause polyphenols to become decomposed and oxidized during the extraction process. This often results in cinnamon extract powder being reddish in color and the percent concentration of polyphenols being low. Heating time determines the ratio of various polymers being extracted. Heating time also affects the thickness of extraction mixture which then has a direct impact on the downstream filtering process. The temperature of the extraction also affects the level of active polyphenols. In some embodiments, the extraction temperature is between 50° C. and 100° C. Optionally, the extractions temperature is between 50° C. and 95° C. Optionally, the temperature is between 50° C. and 90° C. Optionally the extraction temperature is between 50° C. and 90° C. Drying temperature may vary from 75° C. to 120° C. depending on what other extraction parameters are also used. The amount of solvent used is generally from 2 to 100 times the raw extract material on a weight basis. Illustratively, when 50 g of cinnamon bark is used, the extraction is performed with 1000 ml of water (1 g/ml is weight of water—i.e. 20 times volume).

Extraction time is also important for obtaining the desired amount of type-A polyphenols. Extractions are optionally performed by heating the raw material in an extraction solvent in excess of 10 minutes, optionally, in excess of 1 hour, optionally between 1 and 3 hours with any subdivision also operable.

Extraction solvents are optionally aqueous or organic. Distilled water or alcohols such as ethanol are optionally used alone or in combination as extraction solvents. The extracts obtained are optionally water soluble.

Illustrative examples of cinnamon extracts are found in U.S. Pat. No. 6,200,569.

In some embodiments, 50 g clean cinnamon bark is ground into small particles or powder. The powder or particles are mixed with 1000 ml distilled water in a suitable flask. The mixture is let stand at room temperature for about 0.5 hour. In this and other examples, an amount of buffer is optionally added to maintain the pH of the extraction solvent. Additional water may be added is in the range of 1:20 to 1:2000. Too little water may render the mixture too thick for extraction. However, too much water increases drying time. Then the water mixture is heated while being stirred through the use of a magnetic heat stirrer. The temperature and extraction time are crucial to the concentration efficiency of the bioactive polymers. The extraction process is optionally no longer than one hour. Optionally, the ground bark may be heated for 15-20 minutes bringing to a boil, simmering for 20-30 minutes while stirring constantly. Optionally, the ground bark is heated to 100° C. 15-20 minutes and then simmered for 20-30 minutes while stirring constantly. The boiling time is optionally controlled at about 20-25 minutes following heating. The mixture is cooled and stored at 4° C. overnight. An exemplary cinnamon extract obtained by a water extraction is sold as Cinnulin PF by Integrity Nutraceuticals (Spring Hill, Tenn.).

In one embodiment, 250 kg of *Cinnamomum burmannii*, is ground into small particles or powder. The powder or particles are mixed with 2000 ml (8×) distilled ethanol-water in a suitable flask and the mixture is allowed to stand at ambient temperature for 0.5 hours. Optionally, water alone is used as the extraction solvent illustratively by using a 10× fold-water volume/weight ground cinnamon bark. The mixture is heated to 50° C. while being stirred through the use of a magnetic heat stirrer and circulated for 120 min. Evaporation is performed at a steam temperature of less than 100° C. with a process temperature of less than 60° C. with a TS refract meter of 45-50%. The material is then dried to a moisture content of less than 5%. Examples of extracts obtained from the procedures taught herein include Cinnulin PFO obtained from Nutraceuticals International (Sarasota, Fla.).

In some embodiments, Type-A polyphenols are extracted from cinnamon using the following process: 5 g cinnamon and 100 ml 0.1N acetic acid are combined and autoclaved for 15 minutes. The resultant mixture is cooled, then centrifuged and the precipitate discarded. Four volumes of ethanol/0.1N acetic acid are added to the supernatant and the mixture is stored overnight at 4 C.°. The mixture is screened through a filter. To determine the amount of bioactive polymers the mixture is introduced onto an LH-20 column and washed with 600 ml ethanol/0.1N acetic acid. The desired fraction is then eluted with a 1:1 mixture of acetonitrile and 0.2 N acetic acid. The eluate is then concentrated and introduced onto a HPLC column at 275 nm.

In some embodiments, the initial extraction is performed in the absence of acid. 50 g clean cinnamon bark is ground into small particles or powder and mixed with 1000 ml distilled water/10% ethanol in a suitable flask. Then the water mixture is heated while being stirred through the use of a magnetic heat stirrer. The extraction process is optionally no longer than one hour. Optionally, the ground bark in extraction solvent is heated to a boil for 15-20 minutes, and then simmered for 20-30 minutes while stirring constantly. The boiling time is typically controlled at about 20-25 minutes following heating. The mixture is cooled and stored at 4° C. overnight. It is appreciated that alcohols other than or in addition to ethanol, illustratively methanol, may be used in the extraction procedure as well. When alcohol is used in the extraction solvent is it generally present at 50% or less.

Any one of the extraction solutions (or combinations thereof) described herein is optionally filtered through a filter paper to remove any solid debris. If the solution is too thick for the filter paper, the removal of solids from the solution is optionally done with the use of centrifugation. The resulting supernatant is filtered through medium speed filter paper. The resulting solids are optionally dissolved in 200 mL distilled water, or water/ethanol for a second extraction. The liquid solution containing the solids is mixed and heated for 30 minutes at 80-90° C. and then is filtered to produce a second extraction solution.

In some embodiments, first and second extraction solutions are combined together and poured onto nonstick tray and allowed to dry at 80-90° C. Vacuum-spray dry equipment is optionally used for the drying procedure. The resulting dry cinnamon powder is weighed. An extraction ratio is calculated as w/20×100% with was the weight (g) of the dry cinnamon powder. The sample and water ratio, heat time, volume of water in the second extraction may vary depending on the amount of the raw material used for extraction.

High performance liquid chromatography (HPLC) is optionally employed to analyze the effect on the concentrations of the polymers by changes in heating temperature and extraction time. As a non-limiting example, 100 mg dry cinnamon powder is dissolved with 100 ml water in a flask. The solution is sonicated for 30-45 minutes and filtered through 0.45 µm PTFE syringe. The samples are prepared and tested at different temperatures as follows: samples are extracted at 50-60° C. for one hour, Type-A polymers eluting at 17 and 21 minutes have reasonable concentrations. After increasing the temperature to 75-82° C. for 1 hour, the peaks eluting at 17 and 21 minutes are decreased by 2-3%. There are additional two relatively small peaks that seem to surface during this extraction. They elute at 28.5 minutes, 33.5 minutes respectively. After the heating temperature is increased to 85-90° C. for an additional 1 hour, the peaks eluting at 17 and 21 minutes are decreased about 7-9%. The peaks at 28.5 and 33.5 increase significantly. Lastly, the heating temperature is increased to 95-100° C. for 20 minutes and then reduced to 85-95° C. for an additional 40 minutes. The peaks eluting at 17 and 21 minutes seem to decrease by 15-20%. The peaks eluting at 28.5 and 33.5 minutes increase by more than double. According to these results, the polymers at 17 and 21 minutes are converted to isomers at 28.5 and 33.5 minutes respectively. These results suggest that the extraction at 100° C. is suitable to yield acceptable concentration of polymers.

In another procedure, the stabilization of the Type-A polymers is analyzed. Various extraction periods at heating temperature of 50-100° C. are tested particularly 95-100° C. After samples are extracted at 50-100° C. for one hour, polymer eluting at 17 and 21 minutes presents desirable concentrations. The peaks eluting at 17 and 21 minutes decrease as the heating temperature increases in the first 2-3 hours. After 3 hours, the peaks eluting at 17 and 21 minutes no longer change as significantly and seem to reach a plateau period. These results suggest that after a 3 hour extraction time at temperature of 95-100° C., polymers are stabilized.

Not only is it important to note that the time and temperature play a key factor in sustaining higher concentrations of these Type-A polymer key actives, additionally the species of choice can have a dramatic impact on the levels of these Type-A polymers. After thorough review of the world's many species of cinnamon, the following has proven to provide the highest level of active Type-A polymers: *Cinnamomum Burmannii* (Nees) Blume—Microbial Identification Index (MIDI) class; Korintji Cassia.

Cinnamon extract dry power prepared as discussed above is tested to confirm the presence of certain amount of polyphenols such as double-linked polyphenol Type-A polymers, singly-linked Type-A polymers, or other bioactive polymers through the use of HPLC. This allows for standardization of the extract.

In particular instances, the dry weight of the cinnamon extract powder can be standardized on the basis of a bioactive component, such as the doubly-linked polyphenol Type-A polymers. The amount of polyphenol Type-A polymers or the like is optionally in the range of 0.5% to 25%, optionally 1% to 10% by weight. Optionally, the amount of polyphenol Type-A polymers is greater than 0.5%, greater than 1%, greater than 2%, greater than 3%, greater than 4%, greater than 5%, or greater than 10% by weight.

Cinnamon bark may be used in the form of raw bark, sliced, or minced bark, or pulverized bark for the preparation of the therapeutic materials, and pulverized cinnamon bark is used in particular instances.

In one experimental series, an extract is prepared according to the foregoing procedures using a water extraction solvent. The concentration of the sample is approximately (e.g. within error) 5.17 mg/ml. It is also very important to note that the concentrations of the polymers change with the temperature and extraction time.

Depending on the intended mode of administration, the cinnamon extract supplement can be in pharmaceutical compositions in the form of solid, semi-solid or liquid dosage forms, such as, for example, tablets, suppositories, pills, capsules, powders, liquids, or suspensions, and may be provided in unit dosages suitable for a single administration. Time release preparations are specifically contemplated as effective dosage formulations. The compositions will include an effective amount of the selected substrate in combination with a pharmaceutically acceptable carrier and, in addition, may include other medicinal agents, pharmaceutical agents, carriers, or diluents.

In a solid composition embodiment, conventional nontoxic solid carriers may include, for example, pharmaceutical grades of mannitol, lactose, starch, magnesium stearate, sodium saccharine, talc, cellulose, glucose, sucrose and magnesium carbonate. Liquid pharmaceutically administrable compositions may, for example, be prepared by dissolving or dispersing an active compound with optimal pharmaceutical adjuvants in an excipient, such as water, saline, aqueous dextrose, glycerol, or ethanol, to form a solution or suspension. For example, the pharmaceutical composition may contain minor amounts of nontoxic auxiliary substances such as wetting or emulsifying agents, pH buffering agents, for example, sodium acetate or triethanolamine oleate. Actual methods of preparing such dosage forms are known, or will be apparent, to those skilled in this art; for example, see Remington's The Science and Practice of Pharmacy ($20^{th}$ Edition).

In oral administration embodiments, fine powders or granules may contain diluting, dispersing, or surface active agents. The fine powders or granules may be presented in water or in syrup, in capsules or sachets in the dry state, or in a non-aqueous solution or suspension. Suspending agents may also be included in tablets, which may include binders and lubricants in a suspension. Flavoring, preserving, suspending, thickening, or emulsifying agents may be also included to modify the taste and texture of the composition. The tablets and granules provided for oral administration may further be coated for ease of digestion.

In some embodiments, the cinnamon extract containing dietary supplement composition may be combined with one or more other active agents. An active agent optionally functions synergistically with an extract of cinnamon.

Active agents illustratively include vitamins (such as vitamin A, vitamin B, vitamin C, vitamin D, vitamin E or vitamin K), antioxidants (such as acai, wolfberry, alpha lipoic acid, astazanthin, or fucoxanthin), or other sirtuin enhancers (illustratively resveratrol or polygonum), or any combination of the above.

The cinnamon extract according to the present invention is available as a food additive thereto. Examples include foods in a liquid, semi-liquid, solid, paste, or jelly form.

Processes are provided for enhancing expression of a sirtuin gene or protein in a subject. As used herein, a subject is defined as an organism (such as a human, non-human primate, equine, bovine, murine, or other mammal), or a cell. Illustrative examples of cells include monocytes and other leukocytes, β-cells, adipocytes, or enterocytes, or any other cell that endogenously or exogenously expresses a sirtuin gene.

Cinnamon extract materials are optionally metabolized in the subject to yield a therapeutically effect amount of compound species, namely cinnamon polyphenol such as a Type-A polyphenol, cinnamon oligomer, cinnamon catechin or epicatechin, cinnamon chalcone, and cinnamon MHCP. In particular therapies, each dose of the cinnamon extract supplement is selected so as to deliver into the individual polyphenols in the amount of 0.1 milligrams (mg) to 150 mg of Type-A Polymer per serving or any value or range therebetween, optionally 10-30 mg.

Exemplary Processes

The inventors unexpectedly discovered that administration of a therapeutically effective amount of an extract of *Cinnamonum* as described herein or their equivalents functions in an organism similar to caloric restriction, or to administration of resveratrol. Lagouge et al., *Cell,* 2006; 127:1109-1122, describe the many functions of administration of resveratrol in a mammalian subject. The inventors discovered that the same types of effects are also observed following administration of an extract of cinnamon as described herein or their equivalents. As such, inventive processes are provided for increasing lifespan, reducing or preventing reduction in telomere length normally the result of ageing, preventing or reducing diet induced obesity, as well as for increasing insulin sensitivity in an organism. Inventive processes include administration to the subject an extract of cinnamon as described herein or their equivalents.

Inventive processes include administering to a subject a composition that includes an extract of cinnamon. An extract of cinnamon includes at least 0.5% Type-A polymers by dry weight. In some embodiments, any extract of cinnamon containing at least 0.5% Type-A polymers by dry weight may be included in a composition such as extracts included in a dietary supplement. An extract is or is a part of a dietary supplement composition. An extract is optionally present in a dietary supplement composition at 10%-100% by weight, optionally 20%-50% by weight, optionally 30%-40% by weight, or any value or range between 10% and 100% of the dry weight of the dietary supplement composition.

In a typical regimen, the extract materials are taken orally between one and three times daily; although, other routes of administration may be utilized as noted herein. Also, it should be noted that the extracts of the present invention may be utilized in the form of derivatives. For example, the extracts may be bonded, chemically or physically, to other species and moieties such as synthetic polymers, liposomes, small organic molecules, chitin, chitosan, other biopolymers and the like. In view of the teaching presented herein, still further combinations will be readily apparent to those of skill in the art.

A subject is administered a composition in a dosage so that each dose of the cinnamon extract supplement selected to deliver into the Type-A polymers in the amount of 0.1 milligrams (mg) to 150 mg of Type-A Polymer per serving or any value or range therebetween, optionally 10-30 mg. It is further contemplated that variable dosing regiments are operative in the methods.

While in some instances, a single dose treatment may be effective in producing therapeutic effects, in other instances a treatment period in the range of, for example, six weeks to three or six months or more may be utilized. The composition may be administered orally, parentally, or intravenously by intramuscular, intraperitoneally, by transdermal injection, or by contact with a cell or tissue such as by immersion or other form of contact. Injectables may be prepared in conventional forms, either liquid solutions or suspensions, solid forms suitable for solution or prior to injection, or as suspension in liquid prior to injection or as emulsions.

The dose of the composition may vary depending on the age, weight, general condition of the subject. For example, dosage is in the range of 1-1,000 mg of equivalent of dry cinnamon powder extract per day may be an effective range. The cinnamon extract may also comprise 0.01%-100% of the dry weight of the composition. For example, a cinnamon dietary supplement composition may comprise 20%-50% of the dry weight of the composition.

Administration of a composition will enhance expression of a sirtuin gene or protein in a subject. Illustratively, a sirtuin gene expression is increased as measured by the level of sirtuin mRNA relative to a control such as the absence of composition. Illustratively, sirtuin gene expression is enhanced (e.g. increased) by a value of 5% to 300% or more, or any value or range therebetween. Optionally, sirtuin gene expression is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

The level of sirtuin gene expression may be sirtuin gene specific. Illustratively, expression of the gene encoding SIRT1 is enhanced by a value of 5% to 300% or more, or any value or range therebetween. Optionally, expression of the gene encoding SIRT1 is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

In some embodiments, expression of the gene encoding SIRT2 is enhanced. Illustratively, expression of the gene encoding SIRT2 is enhanced by a value of 5% to 300% or more, or any value or range therebetween. Optionally, expression of the gene encoding SIRT2 is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

In some embodiments, expression of the gene encoding SIRT3 is enhanced. Illustratively, expression of the gene encoding SIRT3 is enhanced by a value of 5% to 300% or more, or any value or range therebetween. Optionally, expression of the gene encoding SIRT3 is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

In some embodiments, expression of the gene encoding SIRT4 is enhanced. Illustratively, expression of the gene encoding SIRT4 is enhanced by a value of 5% to 300% or more, or any value or range therebetween. Optionally, expression of the gene encoding SIRT4 is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

In some embodiments, expression of the gene encoding SIRT5 is enhanced. Illustratively, expression of the gene encoding SIRT5 is enhanced by a value of 5% to 300% or more, or any value or range therebetween. Optionally, expression of the gene encoding SIRT5 is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

In some embodiments, expression of the gene encoding SIRT6 is enhanced. Illustratively, expression of the gene encoding SIRT6 is enhanced by a value of 5% to 300% or more, or any value or range therebetween. Optionally, expression of the gene encoding SIRT6 is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

In some embodiments, expression of the gene encoding SIRT7 is enhanced. Illustratively, expression of the gene encoding SIRT7 is enhanced by a value of 5% to 300% or more, or any value or range therebetween. Optionally, expression of the gene encoding SIRT7 is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

Methods for detecting mRNA expression to determine the presence or extent of sirtuin gene expression are known in the art. Illustratively, sirtuin mRNA is detected and optionally quantified by real-time polymerase chain reaction (RT-PCR as used herein). RT-PCR is optionally coupled to prior synthesis of cDNA from total cellular RNA such as using Superscript II RT which is a reverse transcriptase enzyme produced by Invitrogen, Corp., Carlsbad, Calif. Illustrative protocols for measuring sirtuin gene expression can be found in Crujeiras A B, et al., *Eur J Clin Invest*, 2008; 38(9):672-8 as well as in other sources known in the art.

Expression of a SIRT protein in a subject is optionally enhanced by administration of a composition to a subject. Illustratively expression of the SIRT1 protein is enhanced relative to a control. Illustratively, SIRT1 protein expression is enhanced by a value of 5% to 300% or more, or any value or range therebetween. Optionally, SIRT1 protein expression is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

In some embodiments, expression of SIRT2 protein is enhanced relative to control. Illustratively, SIRT2 protein expression is enhanced by a value of 5% to 300% or more, or any value or range therebetween. Optionally, SIRT2 protein expression is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

In some embodiments, expression of SIRT3 protein is enhanced relative to control. Illustratively, SIRT3 protein expression is enhanced by a value of 5% to 300% or more, or any value or range therebetween. Optionally, SIRT3 protein expression is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

In some embodiments, expression of SIRT4 protein is enhanced relative to control. Illustratively, SIRT4 protein expression is enhanced by a value of 5% to 300% or more, or any value or range therebetween. Optionally, SIRT4 protein expression is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

In some embodiments, expression of SIRT5 protein is enhanced relative to control. Illustratively, SIRT5 protein expression is enhanced by a value of 5% to 300% or more, or any value or range therebetween. Optionally, SIRT5 protein expression is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

In some embodiments, expression of SIRT6 protein is enhanced relative to control. Illustratively, SIRT6 protein expression is enhanced by a value of 5% to 300% or more, or any value or range therebetween. Optionally, SIRT6 protein expression is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

In some embodiments, expression of SIRT7 protein is enhanced relative to control. Illustratively, SIRT7 protein expression is enhanced by a value of 5% to 300% or more, or any value or range therebetween. Optionally, SIRT7 protein expression is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

Detecting and optionally quantifying SIRT protein expression is achieved by many methods known in the art. Illustratively, SIRT protein expression is detected and optionally quantified by enzyme linked immunosorbent assay (ELISA), mass spectrometry, western blot, gel electrophoresis optionally coupled with staining such as by Coomassie brilliant blue or silver stain, or by target specific stains, flow cytometry, immunoprecipitation, or by other method known in the art. In some embodiments, an ELISA is used to detect and optionally quantify SIRT protein expression. For example, ELISA kits for SIRT1 and SIRT2 are available from Enzo Lifesciences, Plymouth Meeting, Pa. Kits for other sirtuins are similarly available from commercial sources. Antibodies directed to SIRT proteins suitable for use in ELISA are available from Santa Cruz Biotechnology, Santa Cruz, Calif.

Processes of increasing lifespan are provided. Such processes illustratively include administering to a subject an extract of cinnamon in a therapeutically effective amount sufficient to increase the expression of a sirtuin gene or a SIRT protein, optionally SIRT1, SIRT2, SIRT3, SIRT4, SIRT5, SIRT6, SIRT7, or combinations thereof. A therapeutically effective amount is defined as that capable of increasing the expression of a sirtuin protein or a gene encoding a sirtuin protein relative to a control. An extract of cinnamon includes at least 0.5% Type-A polymers by dry weight. In some embodiments, any extract of cinnamon containing at least 0.5% Type-A polymers by dry weight may be included in a composition such as extracts included in a dietary supplement. An extract is or is a part of a dietary supplement composition. An extract is optionally present in a dietary supplement composition at 10%-100% by weight, optionally 20%-50% by weight, optionally 30%-40% by weight, or any value or range between 10% and 100% of the dry weight of the dietary supplement composition.

Process of increasing lifespan include administering to an organism a dietary supplement composition including an extract of cinnamon in a dosage so that each dose of the cinnamon extract will deliver into the individual Type-A polymers in the amount of 0.1 milligrams (mg) to 150 mg of Type-A Polymer per serving or any value or range therebetween, optionally 10-30 mg. It is further contemplated that variable dosing regiments are operative in the methods. While in some instances, a single dose treatment may be effective in producing therapeutic effects, in other instances a treatment period in the range of, for example, six weeks to three or six months or more may be utilized. The composition may be administered orally, parentally, or intravenously by intramuscular, intraperitoneally, by transdermal injection, or other contact with a subject. Injectables may be prepared in conventional forms, either liquid solutions or suspensions, solid forms suitable for solution or prior to injection, or as suspension in liquid prior to injection or as emulsions.

The dose of the composition may vary depending on the age, weight, general condition of the user. For example, dosage is in the range of 1-1,000 mg of equivalent of dry cinnamon powder extract per day may be an effective range. The cinnamon extract may also include 0.01%-100% of the dry weight of the composition. For example, a cinnamon dietary supplement composition may include 20%-50% of the dry weight of the composition.

It is appreciated that any dietary supplement or any extract of cinnamon described herein or their equivalents are optionally used in a process to prevent or reduce diet induced obesity.

Preventing or reducing diet induced obesity is optionally measured by measuring the lifespan or average lifespan of an organism to which an extract of cinnamon is administered to. Illustrative measurements of lifespan can be found in Dang W, et al., *Nature*, 2009 Jun. 11; 459(7248):802-7; Kaeberlein, M. et al., Genes Dev. 1999; 13(19): 2570-2580; or Rogina and Helfand, *PNAS USA*, 2004; 101:15998-16003. In some embodiments, lifespan is measured by relative telomere length such as telomere length relative to a control subject or other measure of genome integrity that is either measured or known from the literature. A subject with increased average telomere length or other genome integrity relative to a control has a longer lifespan.

Processes of reducing or preventing diet induced obesity are provided. Such processes illustratively include administering to an organism a therapeutically effective amount of an extract of cinnamon. A therapeutically effective amount is defined as that capable of increasing the expression of a sirtuin protein or a gene encoding a sirtuin protein relative to a control. An extract of cinnamon includes at least 0.5% Type-A polymers by dry weight. In some embodiments, any extract of cinnamon containing at least 0.5% Type-A polymers by dry weight may be included in a composition such as extracts included in a dietary supplement. An extract is or is a part of a dietary supplement composition. An extract is optionally present in a dietary supplement composition at 10%-100% by weight, optionally 20%-50% by weight, optionally 30%-40% by weight, or any value or range between 10% and 100% of the dry weight of the dietary supplement composition.

Process of preventing or reducing diet induced obesity include administering to an organism a dietary supplement composition including an extract of cinnamon in a dosage so that each dose of the cinnamon extract will deliver into the individual Type-A polymers in the amount of 0.1 milligrams (mg) to 150 mg of Type-A Polymer per serving or any value or range therebetween, optionally 10-30 mg. It is further contemplated that variable dosing regiments are operative in the methods. While in some instances, a single dose treatment may be effective in producing therapeutic effects, in other instances a treatment period in the range of, for example, six weeks to three or six months or more may be utilized. The composition may be administered orally, parentally, or intravenously by intramuscular, intraperitoneally, by transdermal injection, or otherwise by contact with a subject. Injectables may be prepared in conventional forms, either liquid solutions or suspensions, solid forms suitable for solution or prior to injection, or as suspension in liquid prior to injection or as emulsions.

The dose of the composition may vary depending on the age, weight, general condition of the user. For example, dosage is in the range of 1-1,000 mg of equivalent of dry cinnamon powder extract per day may be an effective range. The cinnamon extract may also include 0.01%-100% of the dry weight of the composition. For example, a cinnamon dietary supplement composition may include 20%-50% of the dry weight of the composition.

It is appreciated that any dietary supplement or any extract of cinnamon described herein or their equivalents are optionally used in a process to prevent or reduce diet induced obesity.

Preventing or reducing diet induced obesity is optionally measured by weighing a subject prior to administering an extract of cinnamon and weighing the subject at one or more times during or following administration of an extract of cinnamon. An organism is optionally fed a diet at least 80% the amount of calories necessary to maintain body weight for an adult. The amount of calories necessary to maintain body weight for an adult will vary depending on the subject's height, weight, age, sex, and exercise level, and is readily determined by one of skill in the art. Illustratively, an organism is a male human fed at least 1700 calories per day. Illustratively, an organism is a female human fed at least 1500 calories per day. In some embodiments an organism is a mouse fed a high fat diet, as is readily determined by those of skill in the art. The weight, body mass index, or other measurement of physical size or density is optionally compared to that of a control subject, to that of the same subject prior to administration, or both.

A process of increasing insulin sensitivity of an organism is also provided. Such processes illustratively include administering to an organism a therapeutically effective amount of an extract of cinnamon. A therapeutically effective amount is defined as that capable of increasing the expression of a sirtuin protein or a gene encoding a sirtuin protein relative to a control. An extract of cinnamon includes at least 0.5% Type-A polymers by dry weight. In some embodiments, any extract of cinnamon containing at least 0.5% Type-A polymers by dry weight may be included in a composition such as extracts included in a dietary supplement. An extract is or is a part of a dietary supplement composition. An extract is optionally present in a dietary supplement composition at 10%-100% by weight, optionally 20%-50% by weight, optionally 30%-40% by weight, or any value or range between 10% and 100% of the dry weight of the dietary supplement composition.

Processes of increasing insulin sensitivity illustratively include administering to an organism a dietary supplement composition including an extract of cinnamon in a dosage so that each dose of the cinnamon extract will deliver into the individual Type-A polymers in the amount of 0.1 milligrams (mg) to 150 mg of Type-A Polymer per serving or any value or range therebetween, optionally 10-30 mg. It is further contemplated that variable dosing regiments are operative in the methods. While in some instances, a single dose treatment may be effective in producing therapeutic effects, in other instances a treatment period in the range of, for example, six weeks to three or six months or more may be utilized. The composition may be administered orally, parentally, or intravenously by intramuscular, intraperitoneally, by transdermal injection, or otherwise by contact with a subject. Injectables may be prepared in conventional forms, either liquid solutions or suspensions, solid forms suitable for solution or prior to injection, or as suspension in liquid prior to injection or as emulsions.

The dose of the composition may vary depending on the age, weight, general condition of the subject. For example, dosage is in the range of 1-1,000 mg of equivalent of dry cinnamon powder extract per day may be an effective range. The cinnamon extract may also comprise 0.01%-100% of the dry weight of the composition. For example, a cinnamon dietary supplement composition may comprise 20%-50% of the dry weight of the composition.

It is appreciated that any dietary supplement or any extract of cinnamon described herein or their equivalents are optionally used in a process to increase insulin sensitivity.

Insulin sensitivity is optionally measured by methods known in the art, illustratively by a hyperinsulinemic-euglycemic clamp technique (DeFronzo, R. A., et al., *Am. J. Physiol.* 237:E214-223, 197) or an oral or intravenous glucose tolerance test (Cutfield, W. S., et al., J. Clin. Endocrinol. Metab. 70:1644-1650, 1990). Other methods known in the art are similarly operable. Insulin sensitivity is optionally increased by 5% or more. Insulin sensitivity is optionally increased by 5% to 200% or more, or any value or range between 5% to 200%.

Various aspects of the present invention are illustrated by the following non-limiting examples. The examples are for illustrative purposes and are not a limitation on any practice of the present invention. It will be understood that variations and modifications can be made without departing from the spirit and scope of the invention.

Example 1: Dietary Supplements

Supplement A:

| | |
|---|---|
| *Cinnamomum burmannii* extract containing not less than (NLT) 0.5% polymers | 200 mg |
| Green Tea 45% egcg | 300 mg |

Supplement B:

| | |
|---|---|
| *Cinnamomum burmannii* extract containing NLT 0.5% polymers | 100 mg |
| *Polygonum cupsidatum* containing 20% resveratrol | 300 mg |

Supplement C:

| | |
|---|---|
| *Cinnamomum burmannii* extract containing NLT 0.5% polymers | 300 mg |
| Alpha Lipoic Acid | 250 mg |
| Vitamin C | 60 mg |
| Vitamin E | 40 IU |
| Acai Berry 4:1 extract | 100 mg |

Supplement D:

| | |
|---|---|
| *Cinnamomum burmannii* extract containing NLT 0.5% polymers | 250 mg |
| Green Tea 45% egcg | 300 mg |
| *Polygonum cupsidatum* containing 20% resveratrol | 200 mg |
| Glutathione | 50 mg |
| Vitamin C | 100 mg |
| selenium | 50 mcg |

Supplement E:

| | |
|---|---|
| *Aronia melanocarpa* 10% anthocyanins | 250 mg |
| *Cinnamomum burmannii* extract containing NLT 0.5% polymers | 500 |

Supplement F:

| | |
|---|---|
| *Cinnamomum aromaticum* extract containing NLT 0.5% polymers | 200 mg |
| Green Tea 45% egcg | 300 mg |

Supplement G:

| | |
|---|---|
| *Cinnamomum aromaticum* extract containing NLT 0.5% polymers | 100 mg |
| *Polygonum cupsidatum* containing 20% resveratrol | 300 mg |

Supplement H:

| | |
|---|---|
| *Cinnamomum aromaticum* extract containing NLT 0.5% polymers | 300 mg |
| Alpha Lipoic Acid | 250 mg |
| Vitamin C | 60 mg |
| Vitamin E | 40 IU |
| Acai Berry 4:1 extract | 100 mg |

Supplement I:

| | |
|---|---|
| *Cinnamomum aromaticum* extract containing NLT 0.5% polymers | 250 mg |
| Green Tea 45% egcg | 300 mg |
| *Polygonum cupsidatum* Containing 20% resveratrol | 200 mg |
| Glutathione | 50 mg |
| Vitamin C | 100 mg |
| selenium | 50 mcg |

Supplement J:

| | |
|---|---|
| *Aronia melanocarpa* 10% anthocyanins | 250 mg |
| *Cinnamomum aromaticum* extract containing NLT 0.5% polymers Plus supplement A | |

Supplement K:

| Cinnamomum verum extract containing NLT 0.5% polymers | 200 mg |
|---|---|
| Green Tea 45% egcg | 300 mg |

Supplement L:

| Cinnamomum verum extract containing NLT 0.5% polymers | 100 mg |
|---|---|
| Polygonum cupsidatum containing 20% resveratrol | 300 mg |

Supplement M:

| Cinnamomum verum extract containing NLT 0.5% polymers | 300 mg |
|---|---|
| Alpha Lipoic Acid | 250 mg |
| Vitamin C | 60 mg |
| Vitamin E | 40 IU |
| Acai Berry 4:1 extract | 100 mg |

Supplement N:

| Cinnamomum verum extract containing NLT 0.5% polymers | 250 mg |
|---|---|
| Green Tea 45% egcg | 300 mg |
| Polygonum cupsidatum containing 20% resveratrol | 200 mg |
| Glutathione | 50 mg |
| Vitamin C | 100 mg |
| selenium | 50 mcg |

Supplement O:

| Aronia melanocarpa 10% anthocyanins | 250 mg |
|---|---|
| Cinnamomum verum extract containing NLT 0.5% polymers | 500 mg |

Example 2: Increase of Sirtuin Expression by Administration of Extract of Cinnamon with Desired Amount of Polyphenols The baseline value for the effects of a high fructose diet on SIRT family mRNA expression is established. The experimental protocols parallel those of Firestein, R., et al., *PLoS ONE*, 2008; 3(4): e2020. doi:10.1371/journal.pone.0002020 except using Wistar rats. The animals fed ad libitum with water and either a standard chow diet or a high fructose diet. Primary enterocytes are obtained from animals (6 months of age) following sacrifice and rapid harvest of the intestine. The isolated intestine is thoroughly flushed with ice cold PBS.

Total RNA is isolated from primary enterocyte tissue obtained as above, adipose tissue (obtained by biopsy), or liver (obtained by biopsy) using TRI reagent (Applied Biosystems, Austin, Tex.), according to the manufacturer's guidelines. The resulting total RNA is subjected to DNase treatment using RNase-free DNase (Ambion). The purity of isolated RNA is measured by a NanoDrop spectrophotometer. A set concentration of RNA is reverse transcribed into cDNA using SuperScript II RT, and quantitative PCR is performed on ABI Prism 7500 Sequence Detection System (Applied Biosystems, Carlsbad, Calif.) using SYBR Green PCR Master Mix (Applied Biosystems, Carlsbad, Calif.).

FIG. 1 illustrates the effects of a high fructose diet on sirtuin mRNA expression. The three graphs show the mRNA expression of genes encoding SIRT1, 2, 3, 5, and 7 in adipose, intestine and liver tissues. The high fructose diet induces a dramatic decrease in the level of mRNA in these three different tissues.

Figure 2:
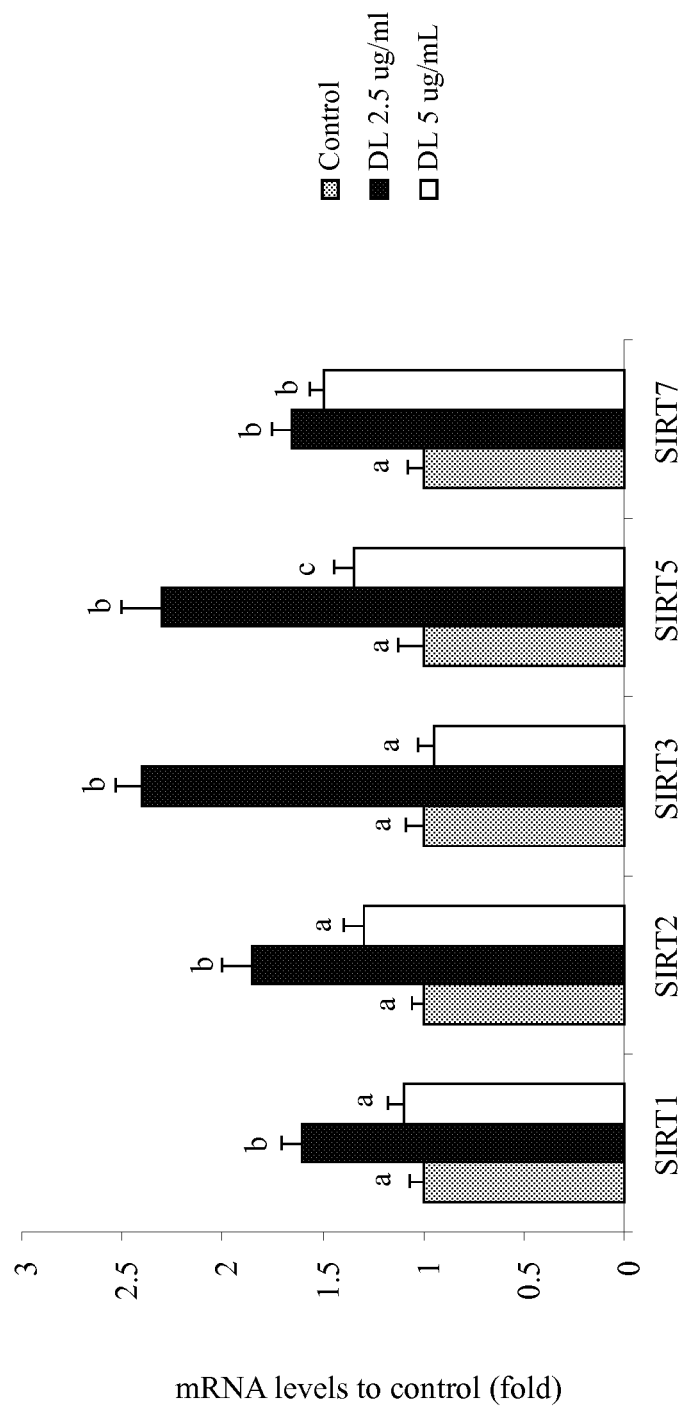
FIG. 2 represents the effects of the anthocyanin delphinidin (DL) from a cinnamon extract on SIRT family mRNA expression in enterocytes of chow-fed rats where a, b, and c represent groupings with $p<0.05$ between groups.

The level of sirtuin mRNA expression is assayed following exposure of rat primary enterocytes to the anthocyanin delphinidin. FIG. 2 illustrates that exposure to the polyphenol delphinidin at 2 µg/ml increases sirtuin gene expression as measured by mRNA levels by 2-3 fold over control. These data indicate that exposure to delphinidin is effective in increasing sirtuin gene expression.

Figure 3:
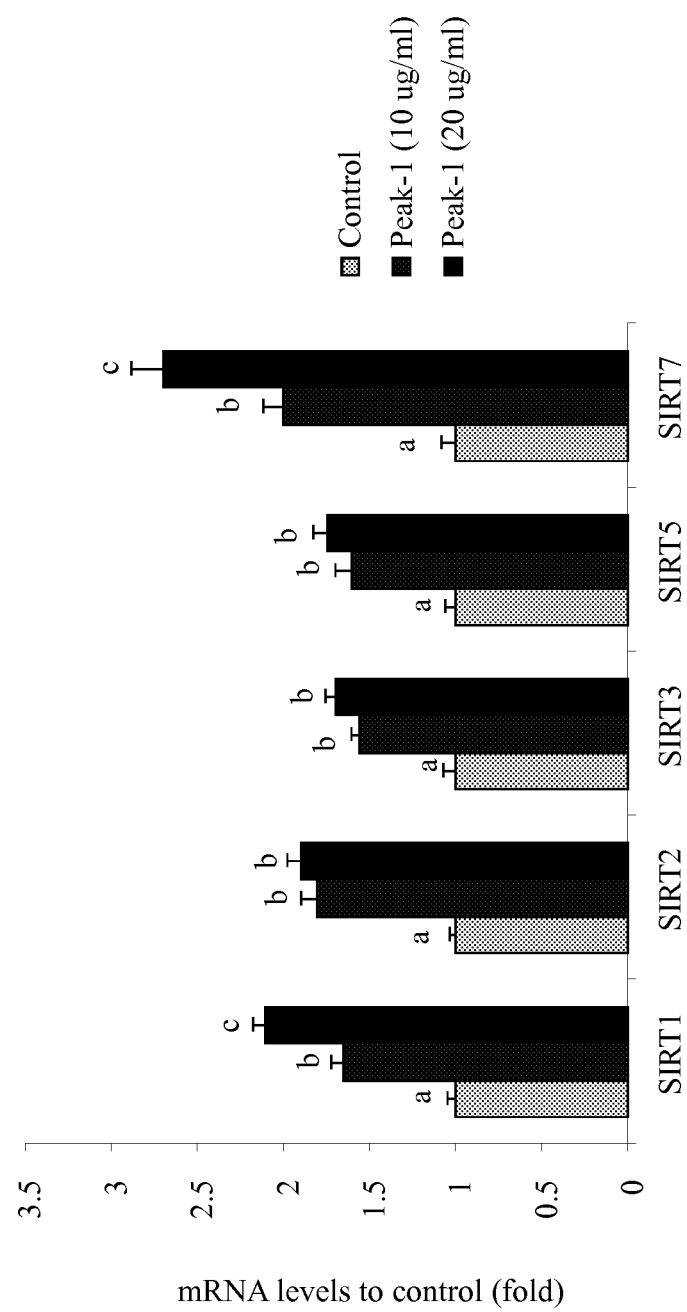
FIG. 3 represents the effects of peak1, doubly linked Type-A polymers from a cinnamon extract on SIRT family mRNA expression in enterocytes of chow-fed rats where a, b, and c represent groupings with $p<0.05$ between groups.

The exposure of a cell to different Type-A polymers is investigated. The polyphenols present in various water soluble water extracts of cinnamon sold as Cinnulin PF by Integrity Nutraceuticals (Spring Hill, Tenn.) are subjected to HPLC isolation and various fractions are designated as peak 1, 2, 3, 4, 5 and peak1-$2^{nd}$. The resulting peak components are then administered at various concentrations in water by contact with rat primary enterocytes obtained as above. As shown in FIG. 3, the administered peak 1 components containing doubly linked Type-A polymers increase mRNA expression in enterocytes of genes encoding SIRT1 (96%), SIRT 2 (77%), SIRT3 (64%), SIRT5 (65%), and SIRT7 (162%). These data establish efficacy of the effects of doubly linked Type-A polymers on the expression of sirtuin family gene expression.

Figure 4:
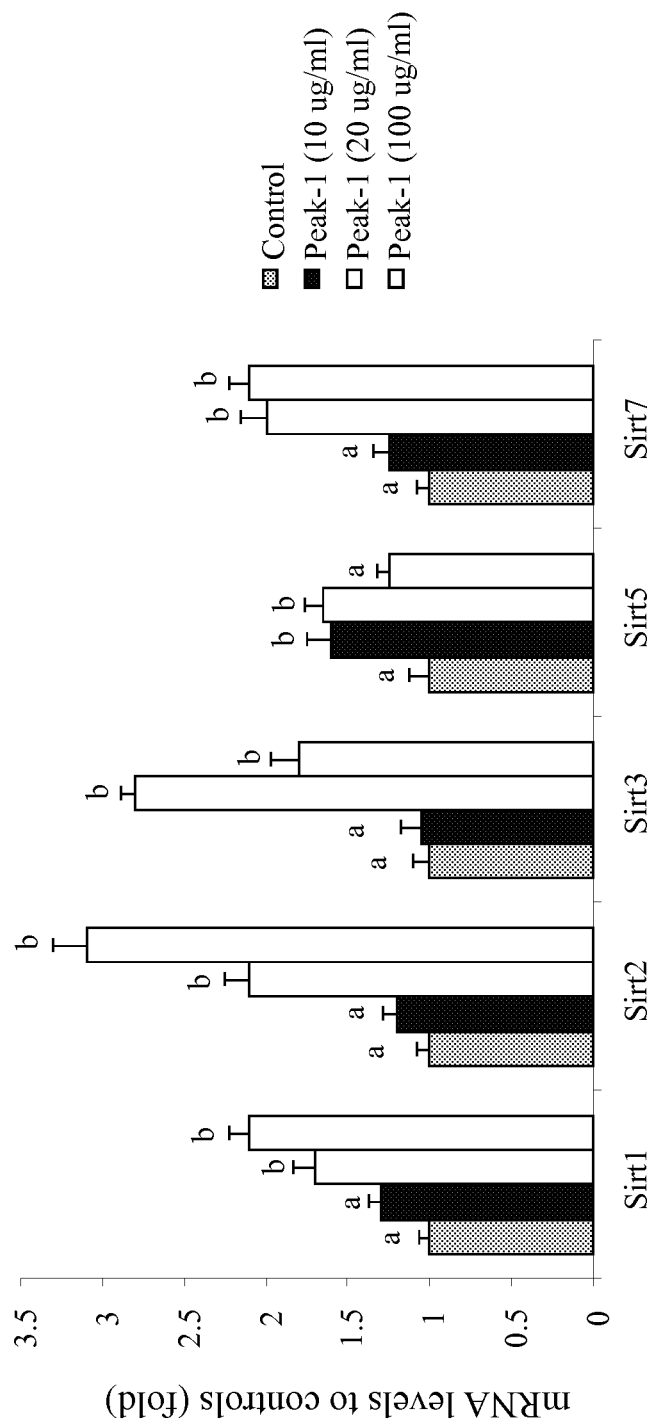
FIG. 4 represents the effects of peak1 of an extract of cinnamon containing doubly linked Type-A polymers on SIRT family mRNA expression in enterocytes of 40 week old chow fed rats where a, b, and c represent groupings with $p<0.05$ between groups.
Figure 5:
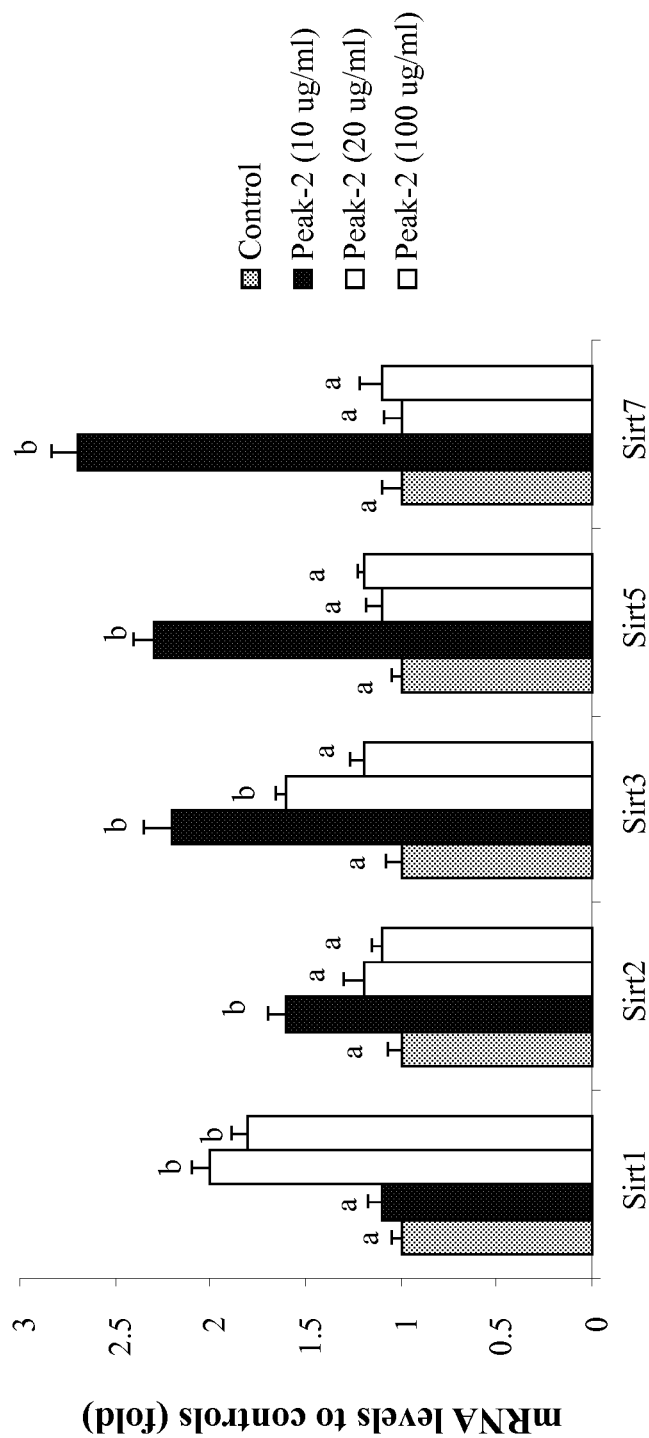
FIG. 5 represents the effects of peak2, doubly linked Type-A polymers from cinnamon extract on SIRT family mRNA expression in enterocytes of 40 week old rats where a and b represent groupings with $p<0.05$ between groups.
Figure 6:
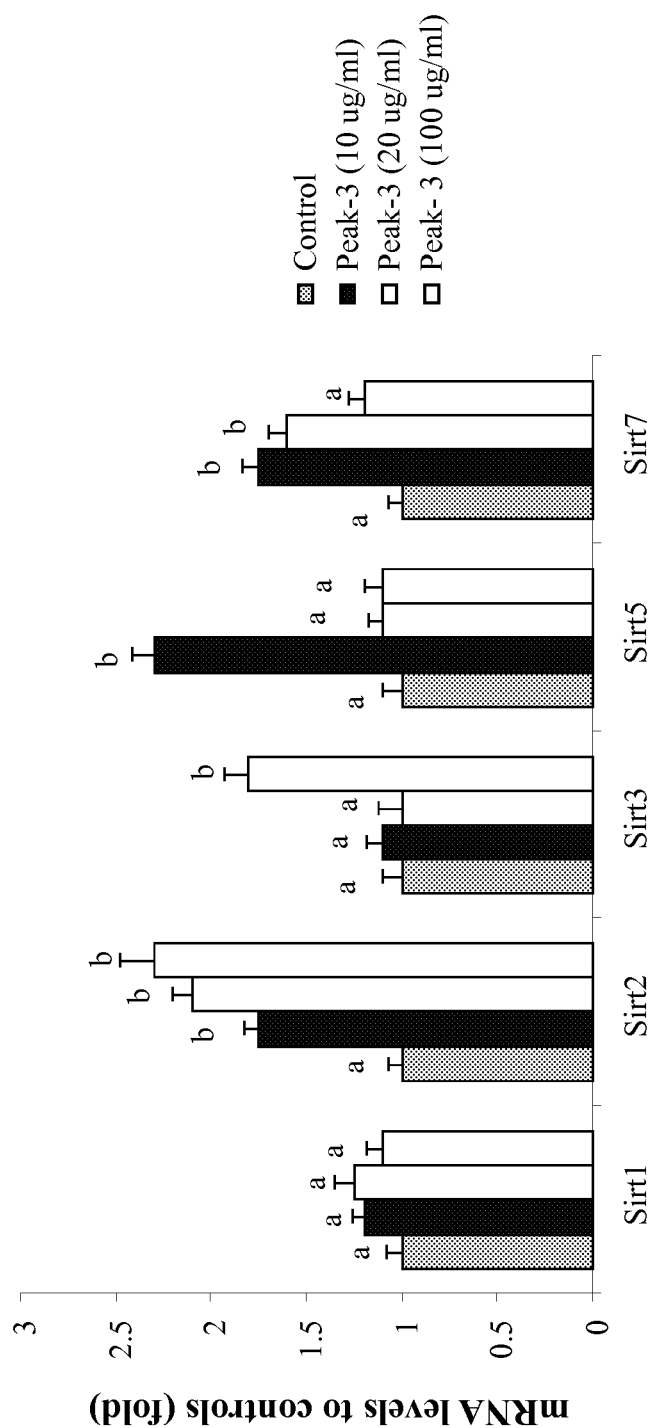
FIG. 6 represents the effects of peak3, doubly linked Type-A polymers from cinnamon extract on SIRT family mRNA expression in enterocytes of 40 weeks old rats where a and b represent groupings with $p<0.05$ between groups.
Figure 7:
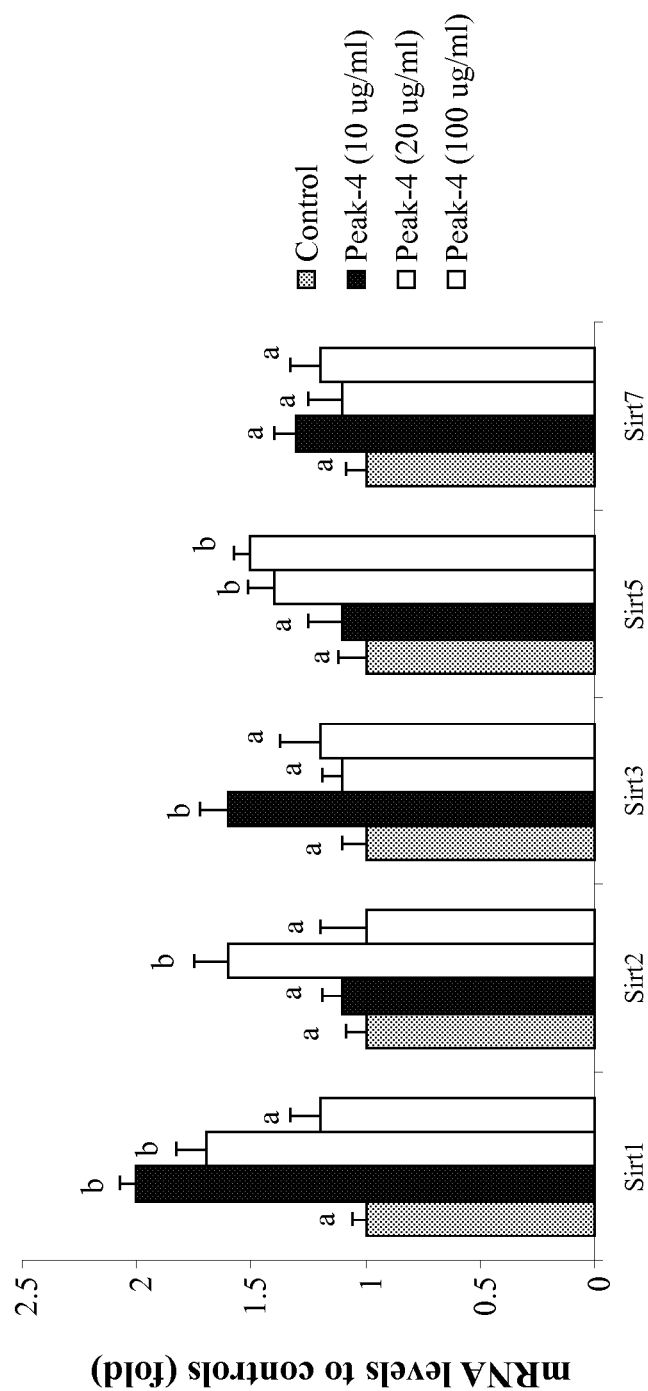
FIG. 7 represents the effects of peak4, doubly linked Type-A polymers from cinnamon extract on SIRT family mRNA expression in enterocytes of 40 week old rats where a and b represent groupings with p<0.05 between groups.
Figure 8:
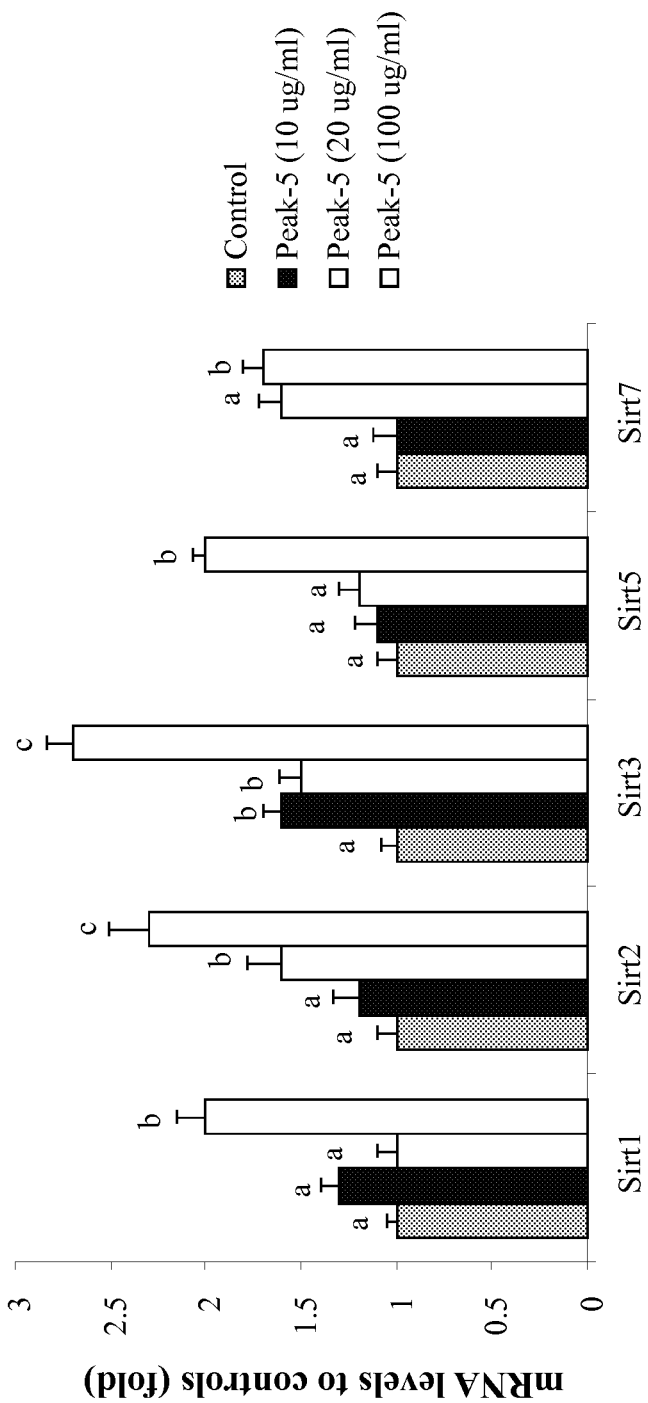
FIG. 8 represents the effects of peak5, doubly linked Type-A polymers from cinnamon extract on SIRT family mRNA expression in enterocytes of 40 week old rats where a, b, and c represent groupings with p<0.05 between groups.
Figure 9:
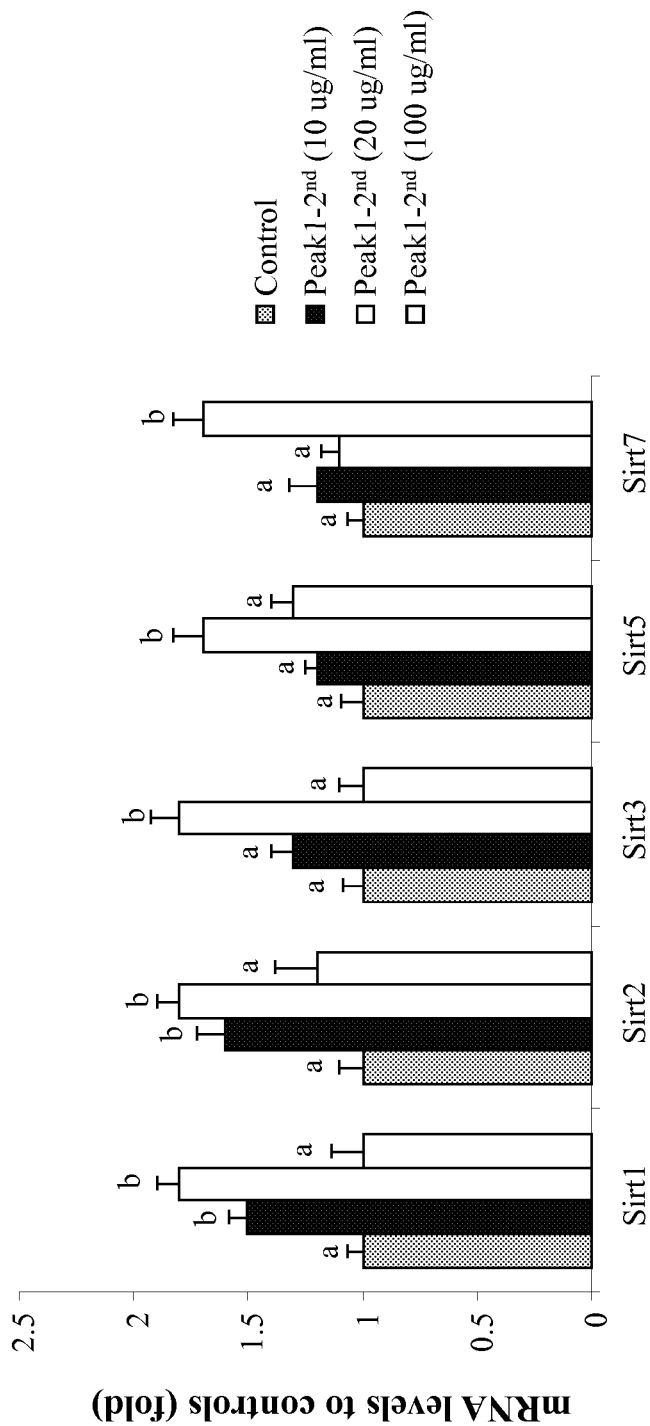
FIG. 9 represents the effects of peak1-2nd, doubly linked Type-A polymers from cinnamon extract on SIRT family mRNA expression in enterocytes of 40 week old rats where a and b represent groupings with p<0.05 between groups.

The studies are repeated using primary enterocytes isolated from 40-week old rats fed a chow diet. FIG. 4 illustrates mRNA expression at a dose of 20 µg/ml of peak 1 polymers increased by: encoding SIRT 1 (80%), SIRT2 (90%), SIRT3 (200%), SIRT5 (60%), and SIRT7 (100%). Increasing the dose of Type-1 polymers generally leads to an increase in sirtuin gene expression.

Similar levels of sirtuin gene expression are observed following administration of purified cinnamon extract peaks containing Type-A polymers at various concentrations. As illustrated in FIGS. 5-9, Type-A polymers from other peaks from the water extract of cinnamon also show increases the expression of genes encoding SIRT1, 2, 3, 5, and 7 as measured by mRNA expression with a similar trends to the peak 1 results.

Figure 10:
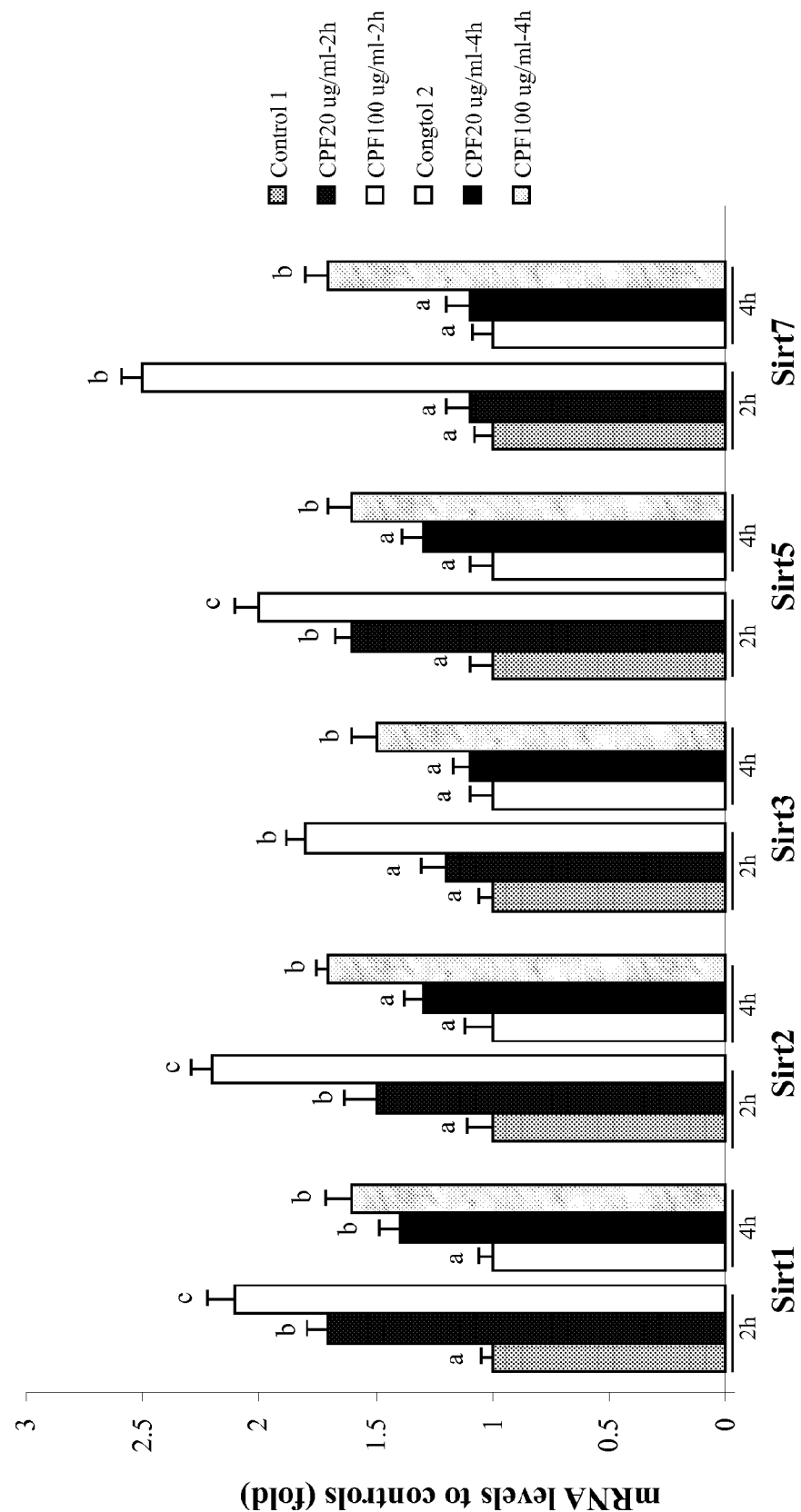
FIG. 10 represents the effects of a water extract of *Cinnamonum* containing doubly linked Type-A polymers on SIRT family mRNA expression in enterocytes of 65 week old rats where a, b, and c represent groupings with p<0.05 between groups.

Primary enterocytes are isolated from rats aged 65-weeks known to have reduced expression of sirtuin genes relative to younger rats. These cells are administered a water extract of cinnamon sold as Cinnulin PF (CPF) at various concentrations for 0, 2, or 4 hours. As shown in FIG. 10, enterocytes from aged rats administered a water extract of cinnamon show a dose-dependent increase in sirtuin gene expression that is observed for genes encoding SIRT1, SIRT2, SIRT3, SIRT5, and SIRT7. These data establish that extracts of cinnamon increase sirtuin gene expression.

The same studies are repeated, but the enterocytes are administered one of supplements A-O. Similar increases of sirtuin gene expression are observed.

Figure 11:
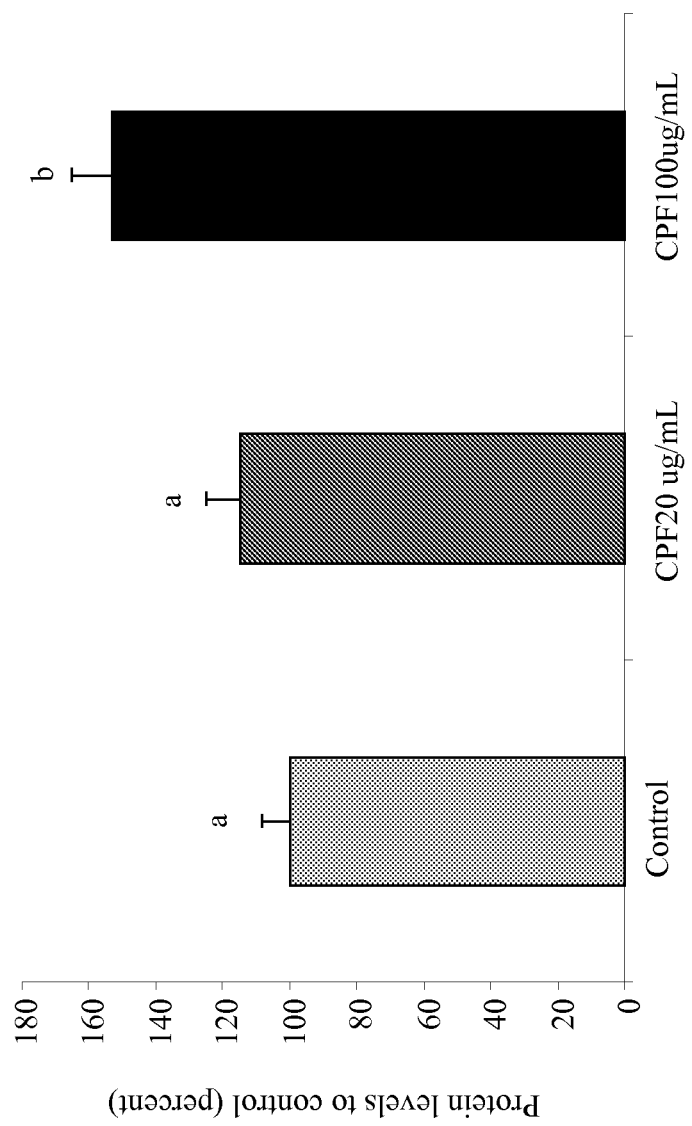
FIG. 11 represents the effects of a water extract of *Cinnamonum* containing doubly linked Type-A polymers on SIRT1 protein expression in enterocytes of 65 week old rats where a and b represent groupings with p<0.05 between groups.
Figure 12:
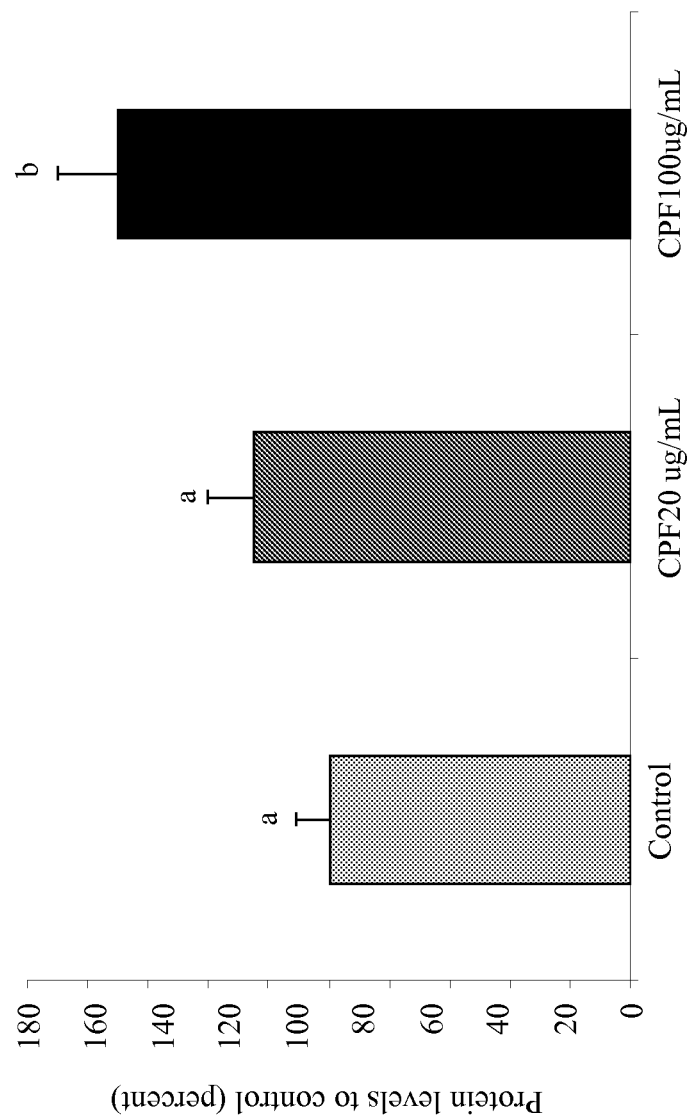
FIG. 12 represents the effects of a water extract of *Cinnamonum* containing doubly linked Type-A polymers on SIRT2 protein expression in enterocytes of 65 week old rats where a and b represent groupings with p<0.05 between groups.
Figure 13:
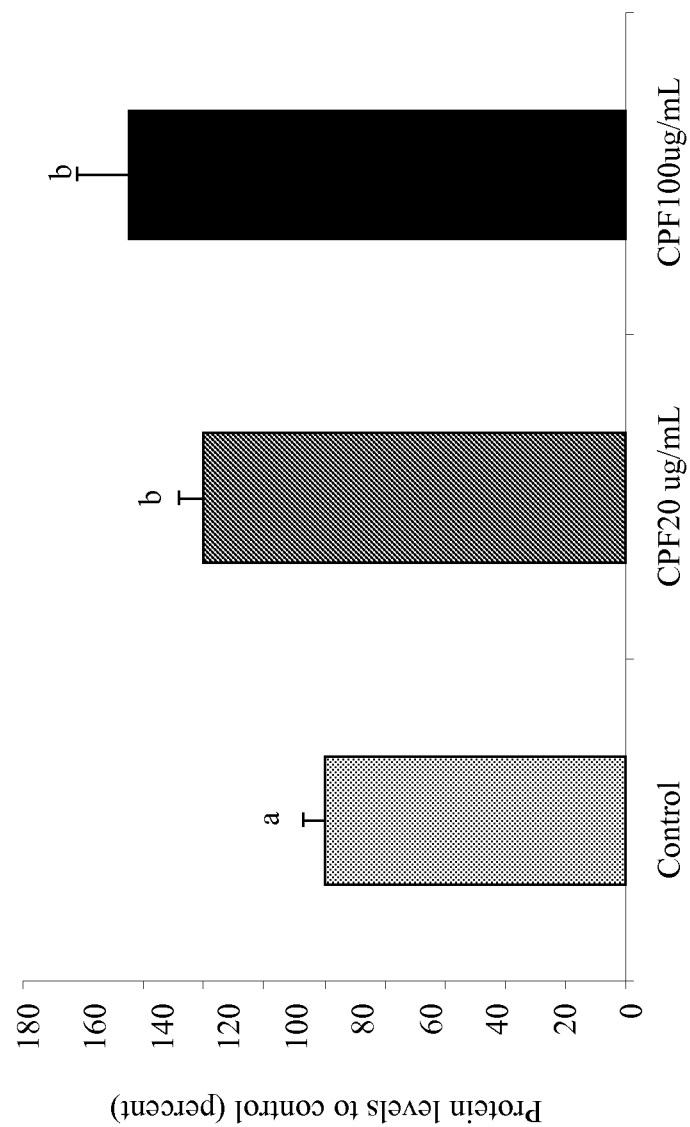
FIG. 13 represents the effects of a water extract of *Cinnamonum* containing doubly linked Type-A polymers on SIRT3 protein expression in enterocytes of 65 week old rats where a and b represent groupings with p<0.05 between groups.

Example 3: Administration of Dietary Supplements Increases Sirtuin Protein Expression Tissue samples are obtained from rats as in mRNA expression studies of Example 2. Tissue samples are homogenized and proteins extracted using T-PER (no. 78510; Thermo Fisher Scientific, Rockford Ill.) along with protease inhibitors and phosphatase inhibitors (Roche). After homogenization, tissue lysates are centrifuged for 30 min at high speed, and supernatant is collected and stored at −70° C. until further analysis. Protein concentrations are measured with bicinchoninic acid protein assay kit (no. 23225; Thermo Fisher Scientific, Rockford, Ill.). A total of 20 µg/lane of protein samples in NuPAGE LDS sample buffer (Invitrogen, Carlsbad Calif.) and reducing agent are loaded into 4-12% NuPAGE Bis-Tris gels (Invitrogen Corp., Carlsbad, Calif.), are subjected to gel electrophoresis, and transferred to polyvinylidene fluoride membranes (GE Healthcare). The membranes are blocked in Tris-buffered saline (TBS) with 3% milk and 0.05% Tween-20 for 1 h at room temperature, washed with TBS-0.05% Tween-20 for 3×5 min, and incubated overnight at +4° C. with primary antibodies (1:1,000) for the various SIRT proteins (Santa Cruz Biotechnology, Santa Cruz, Calif.). The membranes are washed with TBS-0.05% Tween-20 for 3×5 min before incubating them with the appropriate secondary antibody conjugated to horseradish peroxidase (1:40,000) for 2 h at room temperature. The membranes are finally washed with TBS-0.05% Tween-20 for 3×5 min. The bands are visualized using chemiluminescence (ECL plus; GE Health Care), and images are captured in an Image Quant RT-ECL machine (version 1.0.1; GE Health Care). Quantification of the bands is performed by applying Quantity One software (Bio-Rad, Hercules, Calif.). SIRT protein expression is normalized to the level of protein expression in cells not exposed to the composition. As illustrated in FIG. 11, SIRT1 protein is increased between 20% and 60% with 20 µg/ml and 100 µg/ml supplement composition concentration respectively. FIG. 12 illustrates similar results with dose dependent increases in SIRT2 expression. FIG. 13 illustrates similar results with dose dependent increases in SIRT3 expression. Collectively, these results demonstrate that SIRT protein expression is increased in a dose dependent fashion following administration of an inventive extract of cinnamon.

Example 4: Administration of a Cinnamon Extract Containing Dietary Supplement Increases Sirtuin Expression in Animals Rats maintained as in Example 2 are administered a supplement chosen from Supplement A-O diluted in water, or a control (water) by oral gavage once daily for 3 weeks. Prior to and following the test period, primary enterocytes, liver tissue, and fat tissue are obtained from each animal, and the various tissues are assayed for the level of sirtuin gene and protein expression as in Examples 2 and 3 respectively.

Administration of each of Supplements A-O produce an increase in both gene and protein expression by at least 5% for SIRT1, SIRT2, SIRT4, SIRT5, and SIRT7. Similar results are obtained in the primary enterocytes, the adipose tissue, and the liver tissue indicating systemic increases in sirtuin gene and protein expression following administration of a dietary supplement containing a cinnamon extract with at least 0.5% Type-A polymers.

Example 5: Dietary Supplementation with a Water-Soluble Cinnamon Extract Reduces or Prevents Diet-Induced Obesity Six-week-old C57BL/6J male mice are housed on a reverse light-dark cycle in a temperature controlled study area (22±2° C.) with humidity control. The animals are fed either a high-fat diet (HFD) of 4.7 kcal/g energy density (TD 97366, Harlan; 49% fat, 18% protein, 33% carbohydrate) or a standard mouse diet (STD) containing 2.9 kcal/g (A04C, UAR; 8% fat, 19% protein, 73% carbohydrate). Mice are weight matched and assigned to one of the following three groups: high-fat diet fed/vehicle treated (HFD-Veh), high-fat diet fed/cinnamon extract containing supplement D treated (HFD-Supp), and standard diet fed/vehicle treated (STD-Veh). Body weight and individual food intake are recorded daily. The energy intake is determined taking into account the caloric density of each diet and the average daily energy intake is calculated weekly for each of the 5 wk of treatment. To balance the difference in body weight between the groups, the relative energy intake is calculated by correcting for body weight and is expressed as kilocalories per gram mouse per day×100. After a 30-day treatment or oral administration once daily, body fat and lean masses are estimated using a small research animal body composition analyzer (model SA-3000, EM-SCAN) in anesthetized mice.

The mice on a HFD diet treated with vehicle (water) show significantly increased body weight and reduced lean muscle mass relative to animals in the STD-Veh group. Administration of Supplement D once daily for the study period shows a reduced overall weight as well as an increase in lean muscle mass relative to control on the same diet. The experiments are repeated using Supplements A-C and E-O of Example 1. Similar results are obtained compared to the studies with Supplement D.

Example 6: Increased Insulin Sensitivity is Observed Following Administration of Supplement Experiments are performed in insulin-resistant 7-wk-old male F-DIO rats weighing 250-350 g (Levin et al., *Am J Physiol Regul Integr Comp Physiol*, 2003; 285:R1184-R1191). To induce insulin resistance in these animals, F-DIO rats are fed a high-energy diet (HE) containing 15.5% fat and 27.8% sucrose (42 g butter fat, 113 g corn oil, and 278 g sucrose per kg diet).

Three study groups are created (8 rats/group) treated for 4 or 8 wk as follows: 1) untreated controls, F-DIO rats fed regular Purina rat chow (no. 5001) serving as normal controls; 2) HE group, rats fed the HE diet that serve as the insulin-resistant models; and 3) Supplement+HE group, rats fed HE diet and administered one of Supplement A-O of Example 1 diluted in water, serving as the Supplement-treated, insulin-resistant models. At the completion of the study (after 4 or 8 wk of treatment), a 2-h oral glucose tolerance test (OGTT) is performed after an overnight fast. Glucose is fed at 200 mg (0.2 ml of 1 g/ml glucose solution)/100 g body wt by gavage. Blood specimens are collected from the tail at baseline (t=0 min) immediately before and at 15, 30, 60, 90, and 120 min after the initiation of glucose feeding. Blood glucose concentrations (mg/dl) are determined using an automated glucose oxidase method with an Analox glucose analyzer. Insulin levels (ng/ml) are determined by radioimmunoassay (Linco Research, St. Charles, Mo.) using rat insulin radioimmunoassay kit (no. R1-13K, Millipore).

Glucose tolerance is improved in the insulin-resistant rat model (HE-fed F-DIO rats) treated with each of the supplements of Example 1 relative to the controls. Glucose vs. insulin levels are plotted and analyzed by linear regression analysis where a lower slope indicates increased insulin sensitivity. The slope of the Supplement+HE group is lower than the HE group indicating improvement of insulin resistance.

Example 7: Administration of Supplements Containing Extracts of *Cinnamonum* Increases Lifespan Wild-type *S. cerevisiae* of Dang, W, et al., *Nature*, 2009; 459(7248):802-807 are isolated from exponentially growing cultures in YPD (1% yeast extract, 2% bacto peptone, 2% dextrose) by surface labeling with NHS-LC-Biotin (Thermo Fisher) and affinity purification as previously described by Wyce A, et al., *Molecular cell*. 2007; 27(2):275-288. Exponential growth before each round of sorting is limited to 6-8 doublings. About $4 \times 10^8$ old mother cells are saved for analysis after each round of sorting. Alternatively, daughter cells are separated by the methods of Park, et al., *Methods Enzymol*. 2002; 351:468-77.

Replicative lifespans of yeast strains are determined by micromanipulation and life span analyses as described by Kennedy, et al., *J. Cell Biol*. 1994; 127(6 Pt 2):1985-93 with the following modifications. Prior to analysis, strains are patched onto solid YPD for at least two consecutive days. Cells are then transferred at low density to fresh YPD and allowed to grow for ~3 hr. Virgin daughter cells are then isolated as buds from mother cells and subjected to life span analyses in the presence or absence of at least one of Supplement A-O diluted in media. Each experiment consists of 37-50 mother cells and is carried out at least twice, independently.

Yeast strains incubated in the presence of any of Supplements A-O show increased lifespan as measured by percent viable cells at each generation relative to control.

Similar experiments are performed in *Drosophila* essentially as described by Rogina and Helfand, *PNAS USA*, 2004; 101(45):15998-16003 except that experimental flies are fed normal cornmeal sucrose supplemented with one of Supplements A-O. Briefly, flies are maintained in a humidified temperature-controlled environmental chamber at 25° C. Every 2 days, flies are passed into new vials, and the number of dead flies is counted as described by Rogina, et al., *Science*, 2002; 298:1745. The presence of each supplement increases lifespan of the flies relative to controls.

Studies of increased lifespan as measured by telomere length are also performed in humans. A human population study is performed using in a twelve-week, double-blind, placebo-controlled, randomized group study. Subjects are grouped by age from 60-99 years of age by 5 year increments and randomized to receive either a water extract of cinnamon sold as Cinnulin PF composition, the supplement of any of Supplement A-O, or a placebo supplement for a twelve-week period or for a two year period. Minimal steps are taken to influence subjects' lifestyle changes with regard to diet or exercise.

The telomere length is measured by FISH essentially as described by Canela, et al., *PNAS USA*, 2007; 104(13): 5300-5305. Subjects who received the Cinnulin PF or any of the Supplement A-O show average telomere length greater than control subjects. The difference is more pronounced in the two-year study group. Similarly, the amount of critically short telomeres is reduced in subjects who are administered Cinnulin PF or any of the Supplement A-O relative to control subjects.

Methods involving conventional biological techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Methods of producing and screening antibodies are illustratively found in Monoclonal Antibodies: Methods and Protocols, Albitar, M, ed., Humana Press, 2010 (ISBN 1617376469); and Antibodies: A Laboratory Manual, Harlos, E, and Lane, D. eds., Cold Spring Harbor Laboratory Press, 1988 (ISBN-10: 0879693142).

Additional protocols such as PCR Protocols can be found in A Guide to Methods and Applications Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," Methods in Enzymology vol. 182, and other volumes in this series; Current Protocols in Protein Science, John Wiley and Sons, New York, N.Y.; and manufacturer's literature on use of protein purification products known to those of skill in the art.

It will be appreciated by persons skilled in the art that the present invention is not limited to what has been particularly shown and described herein above.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents and publications mentioned in the specification are indicative of the levels of those skilled in the art to which the invention pertains. These patents and publications are incorporated herein by reference to the same extent as if each individual application or publication was specifically and individually incorporated herein by reference for the entirety of their teaching.

The foregoing description is illustrative of particular embodiments of the invention, but is not meant to be a limitation upon the practice thereof. The following claims, including all equivalents thereof, are intended to define the scope of the invention.

The invention claimed is:

1. A process of increasing expression of a gene encoding a sirtuin in a subject comprising:
   administering to a subject a composition comprising at least 0.5 percent Type-A polymers by weight, said Type-A polymers comprising A-type doubly linked procyanidin oligomers of the catechins and/or epicatechins, and
   increasing expression of a gene encoding a sirtuin in said subject by said step of administering.

2. The process of claim 1, wherein said composition further comprises one or more vitamins, antioxidants, sirtuin enhancers, or combinations thereof.

3. The process of claim 1 wherein the composition is administered orally.

4. The process of claim 2 wherein said vitamin is vitamin A, vitamin B, vitamin C, vitamin D, vitamin E, or vitamin K.

5. The process of claim 2 wherein said antioxidant is alpha lipoic acid, acai, astazanthin, wolfberry, glutathione, or super oxide dismutase.

6. The process of claim 2 wherein the sirtuin enhancer is resveratrol or polygonum.

7. The process of claim 1 wherein said composition is administered daily for a period of twelve weeks or more.

8. The process of claim 1 further comprising quantifying the expression of a sirtuin gene in said subject subsequent to said administering.

9. The process of claim 1 further comprising quantifying the level of a sirtuin protein expression in said subject subsequent to said administering.

10. The process of claim 9 wherein said sirtuin protein is SIRT1.

* * * * *